United States Patent
Alkhaldi

(10) Patent No.: US 11,592,593 B2
(45) Date of Patent: Feb. 28, 2023

(54) MODELING HYDROCARBON RESERVOIRS USING ROCK FABRIC CLASSIFICATION AT RESERVOIR CONDITIONS

(71) Applicant: Saudi Arabian Oil Company, Dhahran (SA)

(72) Inventor: Fawwaz M. Alkhaldi, Dammam (SA)

(73) Assignee: Saudi Arabian Oil Company, Dhahran (SA)

(*) Notice: Subject to any disclaimer, the term of this patent is extended or adjusted under 35 U.S.C. 154(b) by 294 days.

(21) Appl. No.: 16/918,195

(22) Filed: Jul. 1, 2020

(65) Prior Publication Data
US 2022/0003891 A1    Jan. 6, 2022

(51) Int. Cl.
G01V 99/00    (2009.01)
G06F 30/10    (2020.01)

(52) U.S. Cl.
CPC ............ G01V 99/005 (2013.01); G06F 30/10 (2020.01)

(58) Field of Classification Search
CPC ........ G01V 99/005; G06F 30/10; G06F 30/00
See application file for complete search history.

(56) References Cited

U.S. PATENT DOCUMENTS

| | | |
|---|---|---|
| 3,975,157 A | 8/1976 | Smith |
| 4,093,420 A | 6/1978 | Grayson et al. |
| 4,606,227 A | 8/1986 | Walters |
| 4,729,960 A | 3/1988 | Foote |
| 7,487,047 B2 | 2/2009 | Wood |
| 9,097,821 B2 | 8/2015 | Skalinski et al. |
| 9,134,457 B2 | 9/2015 | Hurley et al. |
| 10,394,976 B2 | 8/2019 | Adelinet |
| 2003/0231017 A1* | 12/2003 | Kiesl ...................... E21B 49/008 324/303 |
| 2010/0154514 A1 | 6/2010 | Algive et al. |
| 2013/0325349 A1 | 12/2013 | Bunting et al. |
| 2017/0248011 A1* | 8/2017 | Craddock ............ G01N 33/241 |

(Continued)

FOREIGN PATENT DOCUMENTS

| | | |
|---|---|---|
| EP | 2802907 | 11/2014 |
| WO | WO 2009126881 | 10/2009 |

(Continued)

OTHER PUBLICATIONS

Lokier, Stephen W. "The petrographic description of carbonate facies: are we all speaking the same language?" 2016, Sedimentology, 63 pg. 1843-1885 (Year: 2016).*

(Continued)

*Primary Examiner* — Rehana Perveen
*Assistant Examiner* — Troy A Maust
(74) *Attorney, Agent, or Firm* — Fish & Richardson P.C.

(57) ABSTRACT

A rock fabric classification for modeling subterranean formation includes receiving petrophysical properties from a core analysis of a core sample from a wellbore, receiving a core description of the core sample, the core description comprising sedimentological properties of the core sample, determining one or more groups of core samples with similar sedimentological properties and similar core descriptions, determining bounds for each of the one or more groups, providing the bounds and an identifier of each of the one or more groups, as input to a model for petrophysical rock typing or saturation modeling.

23 Claims, 21 Drawing Sheets

(56) References Cited

U.S. PATENT DOCUMENTS

2018/0031732 A1    2/2018  Mosse et al.
2018/0347321 A1   12/2018  Hamon et al.
2019/0277114 A9   12/2019  Le Ravalec et al.

FOREIGN PATENT DOCUMENTS

WO    WO 2013106313        7/2013
WO    WO 2016065127        4/2016
WO    WO-2016065127 A1 *   4/2016   ......... G01N 15/0886

OTHER PUBLICATIONS

Choquette et al, "Geologic nomenclature and classification of porosity in sedimentary carbonates," AAPG bulletin, Feb. 1970, 54(2):207-250.

Dunham, "Classification of carbonate rocks according to depositional textures," American Association of Petroleum Geologists, 1962, pp. 108-121, 14 pages.

Embry III et al, "A late Devonian reef tract on northeastern Banks Island, N.W.T.," Bulletin of Canadian Petroleum Geology, Dec. 1971, 19(4):730-781.

Folk, "Practical Petrographic Classification of Limestones," Bulletin of the American Association of Petroleum Geologists, Jan. 1959, 43(1):1-38.

Lucia, "Petrophysical parameters estimated from visual descriptions of carbonate rocks: a field classification of carbonate pore space," Journal of petroleum technology, Mar. 1983, 35(3):629-637.

Lucia, "Rock-fabric/petrophysical classification of carbonate pore space for reservoir characterization," AAPG bulletin, Sep. 1995, 79(9):1275-1300.

Martin et al, "Characterization of petrophysical flow units in carbonate reservoirs," AAPG bulletin, May 1997, 81(5):734-759.

Wentworth, "A scale of grade and class terms for clastic sediments," The journal of geology, Jul.-Aug. 1922, 30(5):377-392.

PCT International Search Report and Written Opinion in International Appln. No. PCT/US2021/039413, dated Oct. 13, 2021, 15 pages.

Zhou et al., "Controls on reservoir quality of Lower Cretaceous tight sandstones in the Laiyang Sag, Jiaolai Basin, Eastern China: Integrated sedimentologic, diagenetic and microfracturing data." Marine and Petroleum Geology 76, Sep. 2016, 26-50, 25 pages.

* cited by examiner

12 ↙ *Prior Art*

| ALLOCHTHONOUS LIMESTONES ORIGINAL COMPONENTS NOT ORGANICALLY BOUND DURING DEPOSITION | | | | | AUTOCHTHONOUS LIMESTONES ORIGINAL COMPONENTS ORGANICALLY BOUND DURING DEPOSITION | | |
|---|---|---|---|---|---|---|---|
| LESS THAN 10% > 2mm COMPONENTS | | | | GREATER THAN 10% > 2mm COMPONENTS | BY ORGANISMS WHICH ACT AS BAFFLES | BY ORGANISMS WHICH ENCRUST AND BIND | BY ORGANISMS WHICH BUILD A RIGID FRAMEWORK |
| CONTAINS LIME MUD (<.03 mm) | | | NO LIME MUD | > 2mm COMPONENT SUPPORTED | | | |
| MUD SUPPORTED | | GRAIN SUPPORTED | | MATRIX SUPPORTED | | | |
| LESS THAN 10% GRAINS (>.03mm <2mm) | GREATER THAN 10% GRAINS | PACK-STONE | GRAIN-STONE | | | | |
| MUDSTONE | WACKESTONE | | | FLOATSTONE | RUDSTONE | BAFFLESTONE | BINDSTONE | FRAMESTONE |

| BASIC POROSITY TYPES | | | | |
|---|---|---|---|---|
| FABRIC SELECTIVE | | NOT FABRIC SELECTIVE | | |
| INTERPARTICLE | BP | FRACTURE | FR | |
| INTRAPARTICLE | WP | CHANNEL* | CH | |
| INTERCRYSTAL | BC | VUG* | VUG | |
| MOLDIC | MO | CAVERN* | CV | |
| FENESTRAL | FE | | | |
| SHELTER | SH | *CAVERN APPLIES TO MAN-SIZED OR LARGER PORES OF CHANNEL OR VUG SHAPES | | |
| GROWTH-FRAMEWORK | GF | | | |
| FABRIC SELECTIVE OR NOT | | | | |
| BRECCIA BR | BORING BO | BURROW BU | SHRINKAGE SK | |

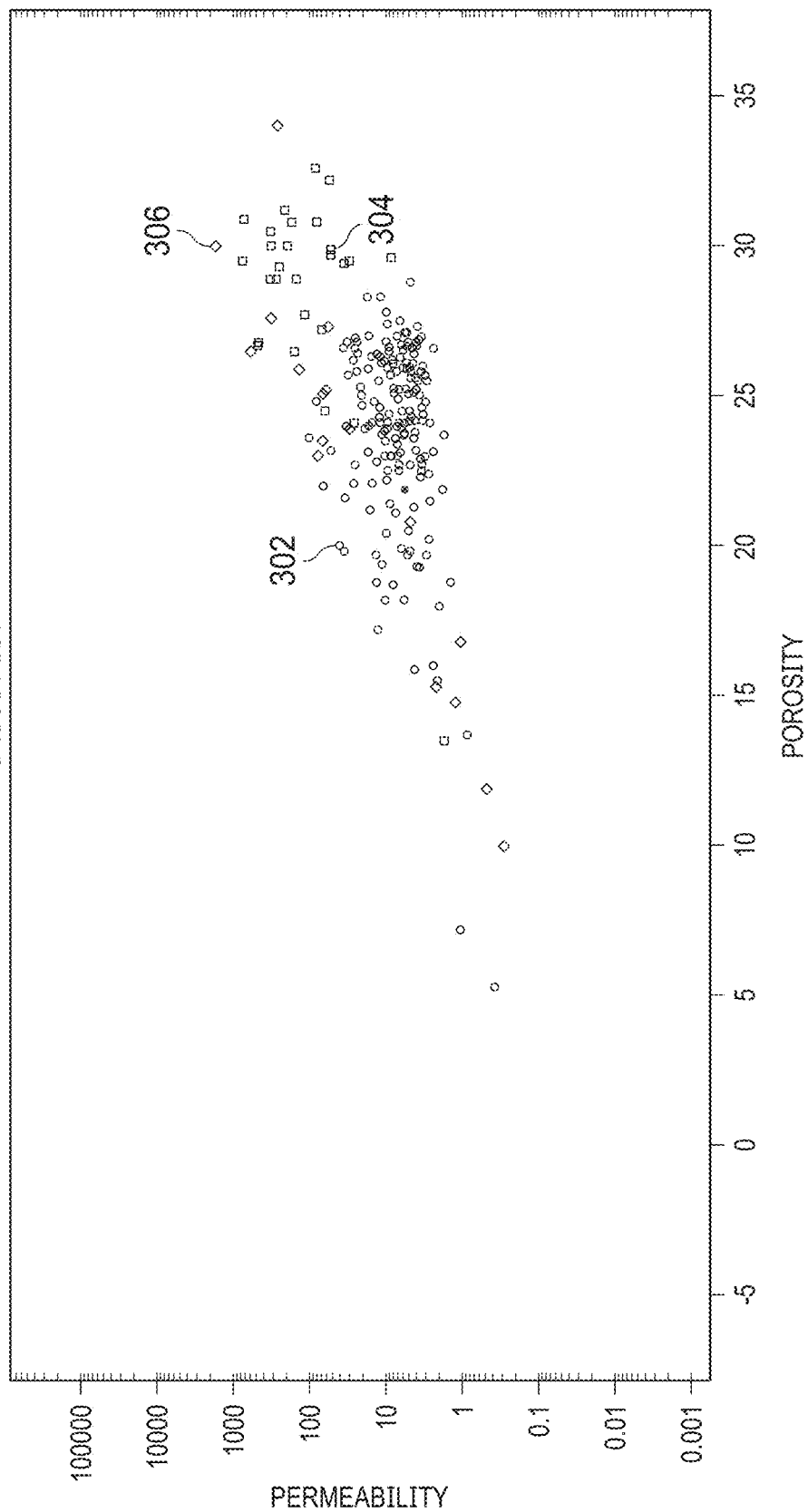

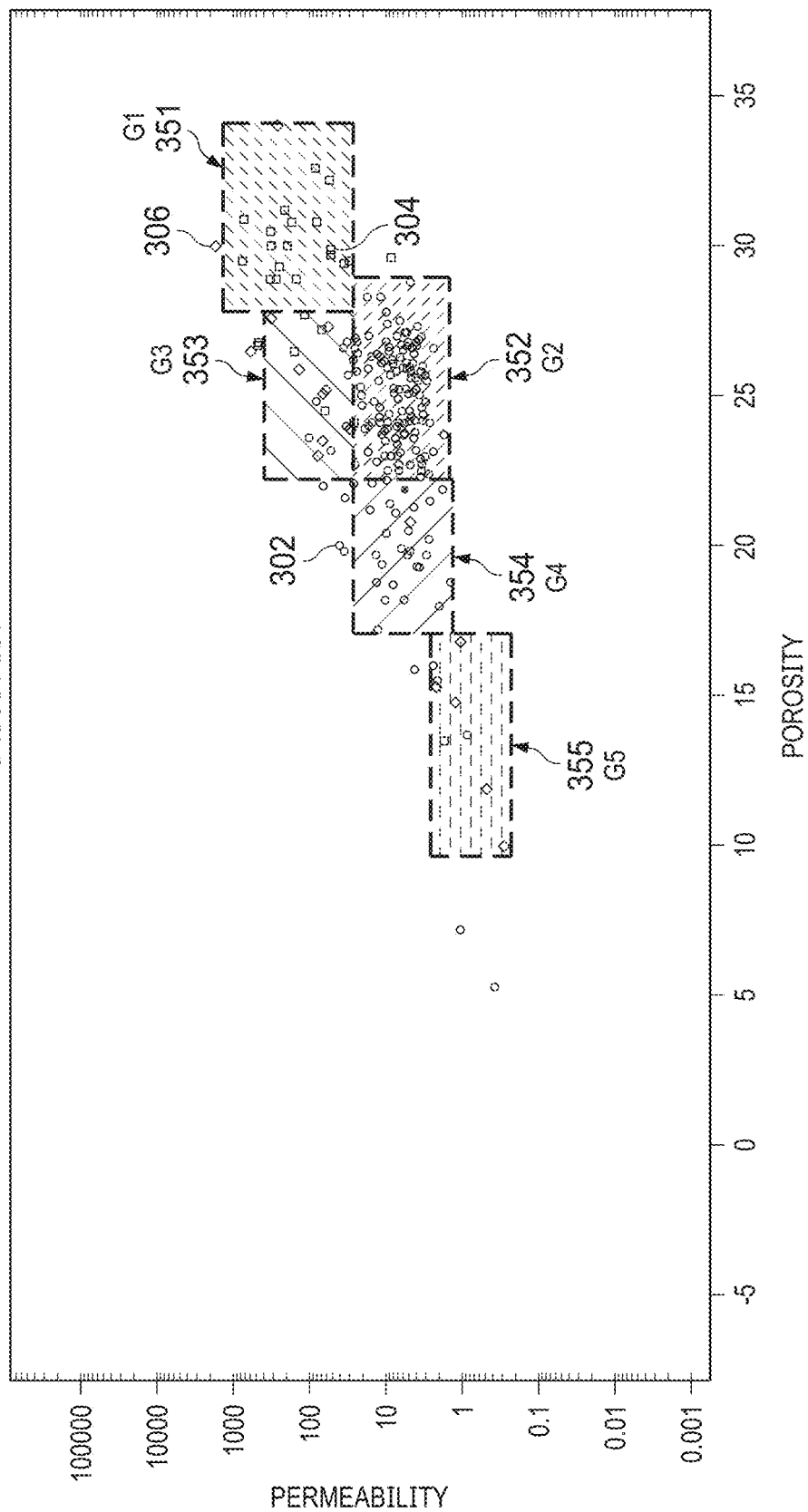

FIG. 12                                                                        850

| Name | Name in the loop | Type | Family | Measurement | Unit | Value | Mode | Description |
|---|---|---|---|---|---|---|---|---|
| 1 EFACIES | efacies | Variable | Classification Gro | | unitless | Lithofacies1 | In | Description |
| 2 Formation | | Number | | | unitless | 2 | | 1=Manifa; 2... |
| 3 PHIT1 | | Number | | | v/v | 0.035 | | Porosity cutoff |
| 4 PHIT2 | | Number | | | v/v | 0.05 | | Porosity cutoff |
| 5 PHIT3 | | Number | | | v/v | 0.06 | | Porosity cutoff |
| 6 PHIT4 | | Number | | | v/v | 0.075 | | Porosity cutoff |
| 7 PHIT5 | | Number | | | v/v | 0.08 | | Porosity cutoff |
| 8 PHIT6 | | Number | | | v/v | 0.09 | | Porosity cutoff |
| 9 PHIT7 | | Number | | | v/v | 0.095 | | Porosity cutoff |
| 10 PHIT8 | | Number | | | v/v | 0.1 | | Porosity cutoff |
| 11 PHIT9 | | Number | | | v/v | 0.115 | | Porosity cutoff |

```
1   import numpy as np
2   from Techlog import MissingValue
3   Loop:
4       if Formation == 1:
5           if efacies == 10:
6               if phit >= PHIT20 and phit < PHIT24:
7                   sub_efacies = efacies + 0.1
8               elif phit >= PHIT24 and phit < PHIT31:
9                   sub_efacies = efacies + 0.2
10              else:
11                  sub_efacies = efacies
12          elif efacies == 9:
13              if phit >= PHIT16 and phit < PHIT22:
14                  sub_efacies = efacies + 0.1
15              elif phit >= PHIT22 and phit < PHIT32:
16                  sub_efacies = efacies + 0.2
17              else:
18                  sub_efacies = efacies
19          elif efacies == 8:
20              if phit >= PHIT15 and phit < PHIT21:
21                  sub_efacies = efacies + 0.1
22              elif phit >= PHIT18 and phit < PHIT25:
23                  if perm >= PERM10 and perm < PERM14:
24                      sub_efacies = efacies + 0.2
25              elif phit >= PHIT21 and phit < PHIT31:
26                  if perm >= PERM14 and perm < PERM18:
27                      sub_efacies = efacies + 0.3
28              else:
29                  sub_efacies = efacies
30          elif efacies == 6:
31              elif phit >= PHIT17 and phit < PHIT23:
32                  sub_efacies = efacies + 0.1
33              elif phit >= PHIT23 and phit < PHIT34:
34                  sub_efacies = efacies + 0.2
35              else:
36                  sub_efacies = efacies
37          elif efacies == 4:
```

MODELING HYDROCARBON RESERVOIRS USING ROCK FABRIC CLASSIFICATION AT RESERVOIR CONDITIONS

TECHNICAL FIELD

This disclosure relates to modeling subterranean formations, particularly modeling subterranean formations using classification and groupings of rock fabric associated with diagenesis.

BACKGROUND

Sedimentologists often produce 3D models, lithofacies maps, and petrophysical studies of subterranean formations to support, for example, hydrocarbon exploration and reservoir management. These models and maps are typically based at least in part on interpreted depositional environment lithofacies that aid in understanding of the depositional behavior and distribution of similar depositional environment rocks. Interpreted depositional environment lithofacies depend on grain types, associated biota, and sedimentary structure along with the depositional texture. The interpreted depositional environment lithofacies can also be associated with more than one rock fabric (for example, bioclastic wackestone to packstone) which results in overlapping regions of different flow characteristics. Multiple rock fabrics can also share similar petrophysical properties even though they can be interpreted to be deposited in different depositional environments.

Classification and grouping of carbonate rock is important for assessing and modeling petrophysical properties of a reservoir. In particular, diagenesis (the physical and chemical changes occurring during the conversion of sediment to sedimentary rock) plays a major role in determining the quality of the reservoir. Diagenesis plays a major role in determining the quality of the reservoir and represents the process of physical and chemical changes in sediments caused by increasing temperature and pressure as the sediments are buried in the Earth's crust. Diagenesis can increase, lower or even eliminate the porosity and permeability of the reservoir, which in turn affects the volume of wells and hydrocarbon flow rates. Natural changes on sediments from the time of deposition are also part of diagenesis. The natural processes producing these changes can be due to compaction, cementation, recrystallization, replacement, differential solution, and authigenesis. Sedimentary and environmental factors stimulating diagenesis include, for example, particle size, pressure, temperature, and chemical conditions.

Before burial, porosity and permeability are controlled by sedimentary conditions and processes. Carbonate deposits are affected by the hydrodynamic energy of water, and the activity level of sea fauna and flora. Most diagenesis occurs during low sea level and exposure of these carbonate rocks to different environments that cause the chemical changes. Porosity can undergo several stages from the time of deposition. The early stages are affected by depositional energy, produced sedimentary structure, and cementation and recrystallization. Later stages are a result of compaction and tectonic activity or an uplift and exposure. Every stage would produce different type of pores and affect the porosity. Pore types can indicate the different stages of porosity evolution and differential solution process.

SUMMARY

This specification describes methods and systems that classify rock fabrics according to a holistic perspective of, among other things, permeability, sedimentological parameters, compaction, pore types, and grain size. This classification is an improvement over previous approaches and is used to extrapolate permeability properties of rocks to un-cored intervals of a well. A model representing the permeability properties of rocks for both cored and un-cored intervals of a well is useful for petrophysists who rely on this information for petrophysical studies. These petrophysical studies include where to locate a well, what depth to extract hydrocarbons from the well, and the hydrocarbons reservoir conditions of the well.

These methods and systems provide an approach to classifying rock fabric that reduces the interpretation biases associated with manual classification by individual sedimentologists. This can be significant because interpreted depositional environment lithofacies can be associated with more than one rock fabric resulting in overlapping regions of different flow characteristics. Multiple rock fabrics can also share similar petrophysical properties even though they can be interpreted to be deposited in different depositional environments. These issues create challenges for petrophysical engineers who are determining the hydrocarbon properties of a reservoir.

For example, medium size ooids grains in grainstone (interpreted as shoals) share the same petrophysical properties as medium size grains of bioclasts grainstone (interpreted as banks). Different grain types may be interpreted as being associated with different depositional environments (e.g., shoals or banks) but they may result in similar petrophysical properties. In another example, an interpreted shoal complex may have a range of rock fabric from packstone to grainstone. Similarly, an interpreted lagoon environment may have a rock fabric range from mudstone to packstone.

Despite these challenges, the methods and systems described in this specification address the issue where a single depositional environment may have petrophysical differences. These differences manifest as a trend on a porosity and permeability cross plot. In contrast, applying conventional interpreted depositional environment approaches to these environments can result in a wide range in porosity and permeability results without a clear trend.

Sedimentary structure is not typically considered when classifying carbonate rocks for petrophysical properties. The described approach considers the occurrence of different sedimentological parameters of the same rock unit with different types and densities. For example, bioturbation is a sedimentological parameter and petrophysically weak burrowed rocks behave differently from intense bioturbated rocks. Stylolites can also occur in different densities in the rock. This process results in reservoir characterization with rock classification and petrophysical rock typing (PRT) which can provide higher quality input for porosity, permeability and saturation modeling than conventional rock classification approaches.

The described approach uses additional rock data than conventional methods that typically address the effect of a single variable (usually the pore throat). Use of the additional data can result in an improved classification of rocks. In addition, the described approach does not require pore throat parameters, which are often hard to measure and usually requires either expensive measurements like Mercury Injection Capillary Pressure (MICP) studies or are estimated using mathematical models.

The present disclosure takes in consideration many of the effective observed parameters including grain size, sorting, pore types, sedimentary structure, dolomitization (i.e., the process by which limestone is altered into dolomite), fractures, and stylolite. These parameters are then analyzed for their effect on porosity and permeability trends. Conventional methods usually do not consider the effect of sedimentary structure in flow units so the present disclosure is considered as an improvement and alternative to the conventional characterization process.

Methods for modeling subterranean formation using rock fabric classification can include receiving petrophysical properties from a core analysis of a core sample from a wellbore, wherein the petrophysical properties include a porosity, a permeability, and a depth of the core sample; receiving a core description of the core sample, the core description including sedimentological properties of the core sample, wherein the sedimentological properties include a grain size and a mud to grain fraction; determining one or more groups of core samples with (i) similar sedimentological properties and (ii) similar core descriptions; determining bounds for each of the one or more groups, wherein the bounds include a lower bound and an upper bound of porosity and a lower bound and upper bound of permeability; and providing the bounds and an identifier of each of the one or more groups, as input to a model for petrophysical rock typing or saturation modeling.

Systems for modeling subterranean formation using rock fabric classification include memory that stores information of one or more core samples from one or more wellbores, the information including petrophysical properties and a core description comprising sedimentological properties; one or more processing devices configured to access the information of the core samples of the one or more wellbores, the one or more processing devices further configured to perform actions including: receiving the petrophysical properties including a porosity, a permeability, and a depth of the core sample; receiving the core description including the sedimentological properties, wherein the sedimentological properties include a grain size and a mud to grain fraction; determining one or more groups of core samples with (i) similar sedimentological properties and (ii) similar core descriptions; determining bounds for each of the one or more groups, wherein the bounds include a lower bound and an upper bound of porosity and a lower bound and upper bound of permeability; and providing the bounds and an identifier of each of the one or more groups, as input to a model for petrophysical rock typing or saturation modeling.

Embodiments of these systems and methods can include one or more of the following features.

Some embodiments also include determining, using the bounds of each of the one or more groups, a rock fabric prediction for an un-cored well or an un-cored well interval.

Some embodiments also include training, using the one or more groups, the rock fabric prediction for the un-cored well or the un-cored well interval.

Some embodiments also include classifying the core sample as a mud-dominate packstone if the carbonite rock fabric (i) comprises grains with the grain size of less a grain size threshold and (ii) comprises the mud to grain fraction in an amount greater than a mud threshold. In some cases, the grain size threshold is less than 1 mm. In some cases, the mud threshold is less than 20%.

Some embodiments also include classifying the core sample as a grain-dominated packstone if the carbonite rock fabric (i) comprises grains with the grain size of greater than the grain size threshold and (ii) comprises the mud to grain fraction in an amount less than the mud threshold.

Some embodiments also include cases where receiving the sedimentological properties represents at least two different described lithologies of the wellbore. In some cases, the sedimentological properties further comprise sorting, pore types, sedimentary structure, dolomitization, fractures, and an amount of stylolite. In some cases, the core description comprises a percentage estimation chart. In some cases, the determining of the one or more groups of core samples is performed manually.

Some embodiments also include cases where the core samples are from a plurality of wellbores.

Some embodiments also include a display configured to display the bounds and the identifier of each of the one or more groups.

The described approach can avoid the uncertainty introduced by conventional classification approaches that are sometimes biased to specific depositional models. In conventional approaches, groups of similar depositional lithofacies can be tested using MICP measurements to statically identify the proper depositional environment, but using interpreted depositional environment lithofacies can also be misleading if the same environment does not have similar behavior on a porosity and permeability plot.

By developing porosity, permeability, and saturation modules for each facies after generating the PRT, the PRT results are understood in a sedimentological sense instead of mathematical sense, since PRTs are mathematically-derived results.

The details of one or more embodiments of these systems and methods are set forth in the accompanying drawings and the description below. Other features, objects, and advantages of these systems and methods will be apparent from the description and drawings, and from the claims.

DESCRIPTION OF DRAWINGS

FIGS. 2A-2C are rock fabric classification charts.

FIG. 9A is a permeability vs. porosity plot of grainstone rock fabric taken from several cored wells. FIG. 9B is a classification of the grainstone rock fabric of FIG. 9A.

FIG. 12 is a screenshot of a script used for the classification.

Like reference symbols in the various drawings indicate like elements.

DETAILED DESCRIPTION

This specification describes methods and systems that support modeling hydrocarbon reservoirs using rock fabric classification at reservoir conditions. These systems and methods incorporate the reclassification of carbonate rock fabric based on sedimentary parameters. This approach identifies carbonate rocks that have similar petrophysical properties (for example, porosity and permeability) as a product of diagenesis. Clustering and grouping these rocks enables a link between different diagenetic controlling factors from the described core to their petrophysical properties of porosity and permeability for better petrophysical rock typing (PRT) and saturation modeling for a better understanding of wellbore properties at reservoir conditions.

Properties such as porosity and permeability of rock fabric are particularly important because they indicate how the rock fabric interacts with fluids, such as hydrocarbons, near wellbores. Porosity is the percentage of a given volume of rock that is pore space and can contain fluids. Permeability is the quantity of fluid that can flow through a rock as a function of time and pressure, and is related to the interconnection of the pores.

Figure 1:
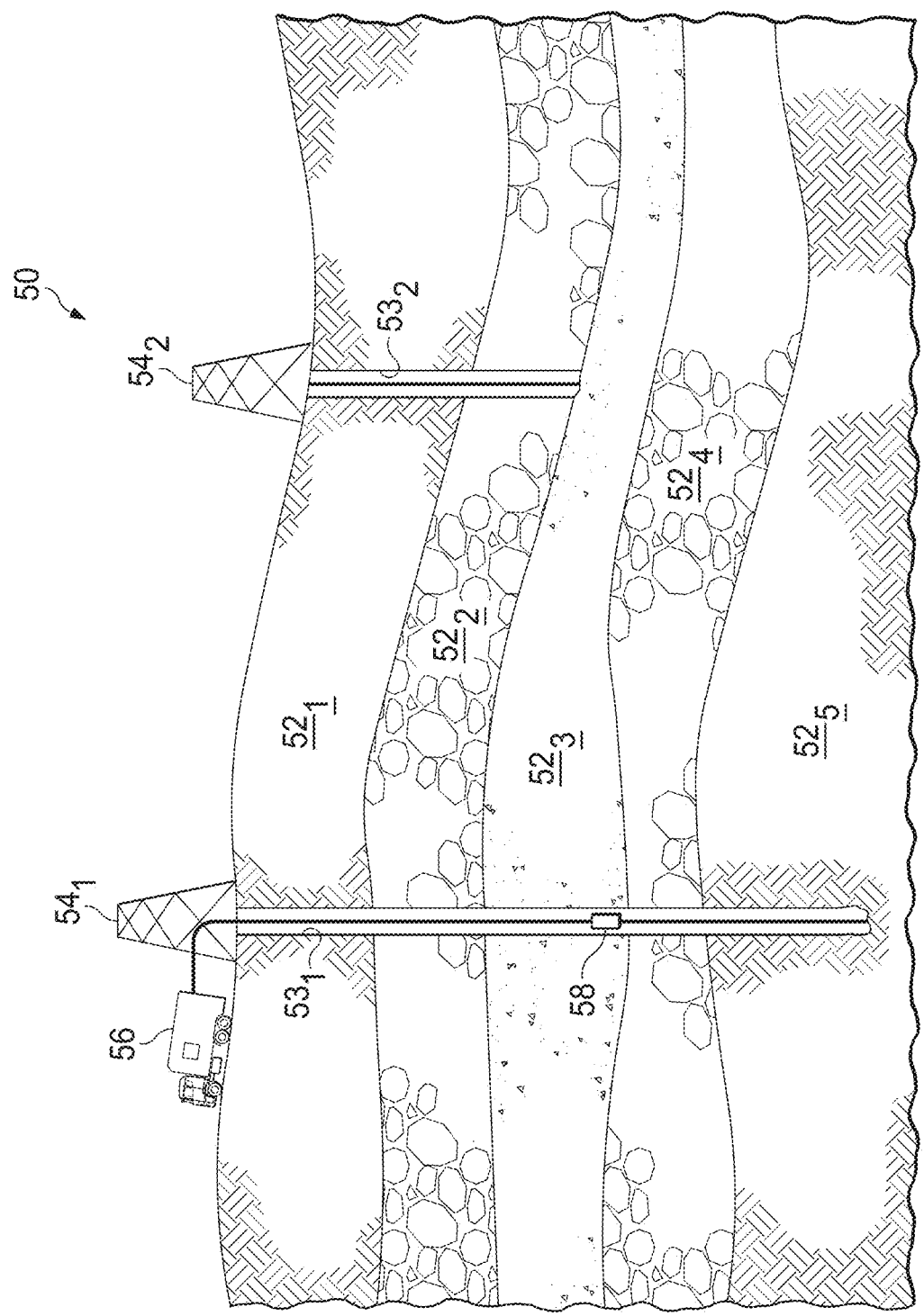
FIG. 1 is a schematic illustrating well bores in a subterranean formation.

FIG. 1 shows a subterranean formation 50 with multiple layers $52_1$, $52_2$, $52_3$, $52_4$, $52_5$. FIG. 1 illustrates two of the many methods of getting information about the properties of the layers $52_1$, $52_2$, $52_3$, $52_4$, $52_5$. A first wellbore $53_1$ extends into the subterranean formation 50 from a first drill rig $54_1$. A logging truck 56 is lowering a logging tool 58 on wireline into the first wellbore $53_1$. The logging tool 58 measures properties of the subterranean formation as the logging tool 58 is lowered down the first wellbore. A second wellbore $53_2$ is being drilled extending into the subterranean formation 50 from a second drill rig $54_2$. During the drilling operation, core plugs are extracted at depth intervals, analyzed, and tested.

By analyzing core plugs, one can classify its rock fabric based on at least some of the sedimentological parameters of the core plug. Quantitative information such as permeability and porosity can be determined by testing the core plug. This approach gives sedimentologists some information about the rock fabric in the wellbore, but not a complete picture. The data from analysis of the core samples is more detailed than the data acquired by the logging tool 58 but is more expensive and time-consuming to generate.

The systems and methods described in this specification provide an approach for determining an improved prediction for the rock fabrics that were not tested (e.g., the rock fabrics that lie between the core plugs that were extracted or the rock fabrics along the well bores which were drilled without extracting core plugs). As a result, a more complete picture interpreted depositional environment and the rock fabric of the wellbore and the nearby subterranean formations is achieved.

The sedimentology and petrophysical properties of a reservoir are important inputs required to build three-dimensional models (petrophysical rock typing (PRT) and saturation modeling). However, determining these properties throughout the reservoir is hard, expensive, and time consuming. Despite sedimentological studies being considered one of the main inputs to a petrophysical analysis, there is no unified scheme in presenting the sedimentological classification. In carbonate rocks, the classification schemes can be based on interpreted depositional environment, a described rock fabric, or a combination of both.

Rock fabric plays an important role in describing carbonate rocks. Currently used classification of interpreted depositional lithofacies cover a wide range of rock fabrics (such as bioclastic wackestone to packstone) which can have different flow properties. Dunham's classification is considered a practical classification for sediments to indicate depositional energy through the identification of mud content and packing of grains. However, Dunham's classification alone can be insufficient to determine flow properties of a rock fabric. Some rock fabrics have similar values of porosity and permeability with the same flow properties.

The present disclosure describes a carbonate classification based in part on Dunham's classification. Once a core plug is received for analysis, the rock fabric is first sorted using Dunham's classification. The rock fabric is then further sorted according to sedimentological parameters. Sedimentological parameters can include grain size, sorting, pore type, sedimentary structure, dolomitization, fracture, and presence of stylolite, but other parameters can be used. Sedimentary structure plays a major role in orientation of grains and flow characteristics of rock fabric. Grain size and sorting can indicate a level of depositional energy. Dolomitization can indicate a degree of replacement or recrystallization. Fracture and stylolite can indicate the compaction and tectonic activity.

This approach produces specific porosity and permeability value ranges for each rock fabric and classifies each rock fabric into clustered regions on a porosity versus permeability plot. A trend, which is usually linear, is observable and this classification is used to re-code the original core description. The trend can be used to estimate the average permeability vs. porosity relationship and further defines a lower permeability limit, upper permeability limit, lower porosity limit, and upper porosity limit of the core plug. After this classification is performed, petrophysical properties of uncored intervals in a wellbore or of uncored wellbores can be assigned extrapolation based on parameters measured by, for example, wireline logging. The predicted properties on these uncored intervals can be used for further petrophysical studies and saturation modeling by petrophysicists.

The plug data is generated as a result of routine core analysis, however, while preferred, the plug data does not need to come from MICP data. MICP is an accurate quantitative technique for measurements of porosity, pore throat size distribution, and injection pressure vs. mercury saturation for many types of rocks but is expensive to perform on each core. The described approach can be validated using MICP to give the benefit of using information from each core along with high accuracy MICP information.

Figure 2A:

FIG. 2A is a flowchart of Dunhams's (1962) classification 10 of carbonate rocks according to depositional texture. Dunham's classification 10 is first used to classify the carbonate rock fabric. Grain-dominated packstone (GDP) and mud-dominated packstone (MDP) are then further classified from Dunham's original rock fabric. The cutoff boundary used for GDP and MDP as follows. GDP is classified when about 10-15% of mud is still present in a grainstone fabric. MDP is classified when about 10-15% of grains are packed and in contact in a wackestone fabric. These ranges are based on Dunham's classification 10 which indicates that wackestone starts when the grains to mud ratio is greater than 10%. Using a 10-15% range reflects that the grains are packed, in contact, and are not floating in the matrix of mud. The lower limit of 10% is used because it is the cutoff for the wackestone according to Dunham. Sometimes other values are used for the upper limit, such as 20%. This upper limit can be defined by a user-preference. These ranges represent the transition between a major classifications and a sub-classification.

FIG. 2B is a flowchart of Embry and Klovan's (1971) classification 12 which is a modification of Dunham's classification 10. Embry and Klovan extended Dunham's classification 10 in the area of Bindstone and Bafflestone and are sub-classifications of Dunham's Boundstone. Both classifications used in the oil and gas industry and the Bindstone and Bafflestone contributions of Embry and Klovan are used in this specification. The rock fabrics follow the same mud to grains cutoff as used by the Dunham classification 10 and extended by the Embry and Klovan classification 12. A grain size chart is used to identify the size of grains. Non-skeletal and skeletal grains size are documented separately. The mud cutoff used in the Embry and Klovan classification 12 can be less than 0.0625 mm size and not as in the original Dunham's classification 10.

FIG. 2C is the Choquette and Pray (1970) classification 14 used to classify the porosity type in the rocks. Identification of different porosity types throughout this specification is guided by using the Choquette and Pray classification 14.

Figure 3A:
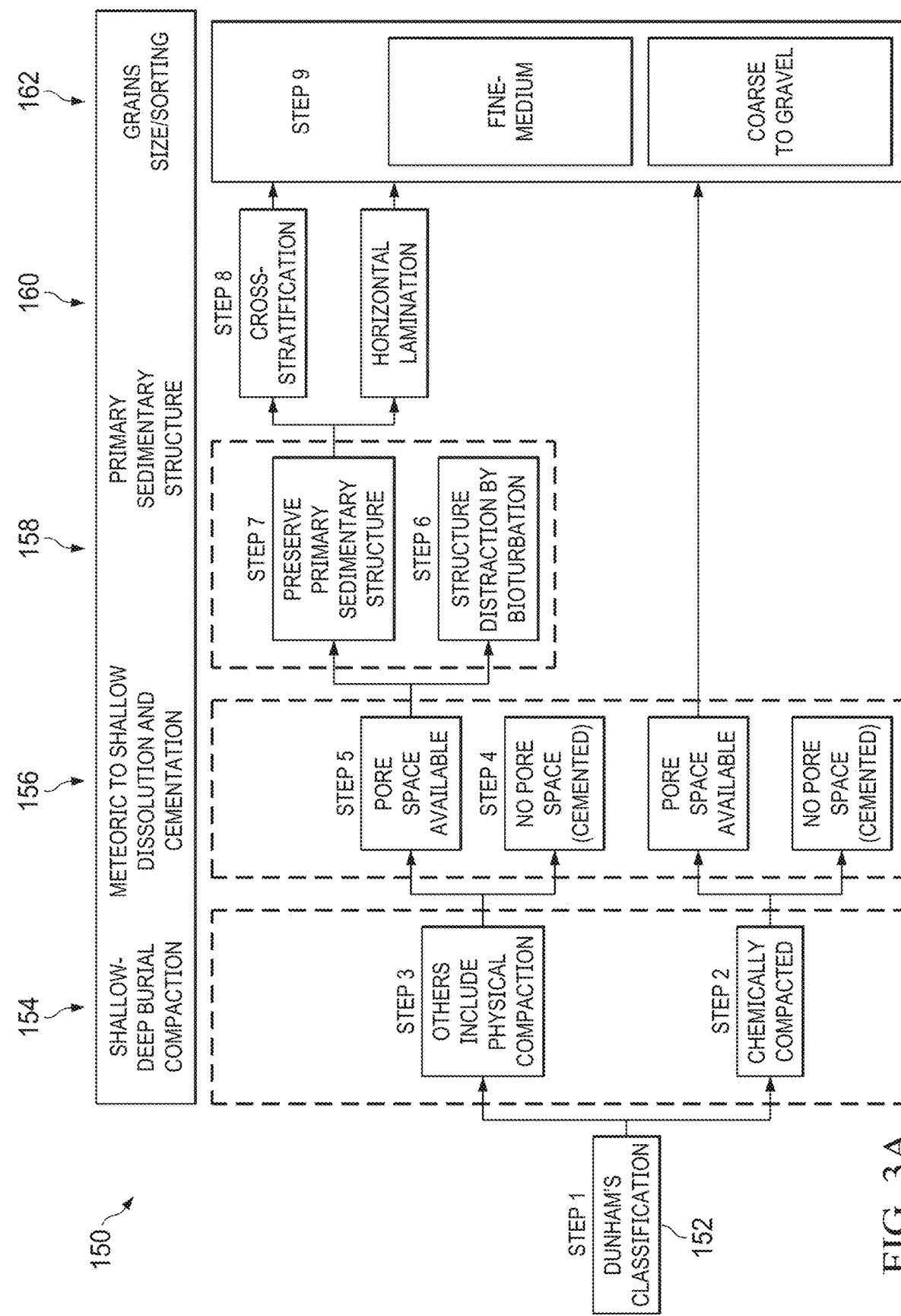
FIGS. 3A-3B are flow charts of methods for rock fabric classification.

FIG. 3A is a flowchart of a method 150 used in the sub-classification. The method 150 sub-divides textures to represent a high to low permeability. The classification uses Dunham's classification 10 because it reflects the energy level and mud-grain content in the rock (step 152). Chemically compacted rocks are separated from non-chemically compacted rocks (step 154). In most cases, wispy lamination and stylolite are the usual chemical compaction features seen in step 154, but other chemical compaction features can be present.

The rocks are investigated in terms of pore types and cementation (step 156). Step 156 represents a diagenetic processes that has occurred in the meteoric and shallow burial realms. In step 156, rocks are separated based on whether or not they show dissolution feature and whether or not they have been subjected to full cementation and have no pore spaces. For example, some dissolution features include moldic porosity (MO), Vugy porosity, and Intraparticle particles porosity (WP). Rocks are sorted based on pore space in terms of whether or not the rocks show preservation of primary sedimentary structure (step 158). For example, in step 158, rocks preserving sedimentary structure, such as cross bedding and parallel lamination, are separated from rocks that show more bioturbation. Bioturbation is considered a diagenetic feature since it occurs after the precipitation of the sediments. Rocks are sorted based on whether or not they show cross stratification or lamination (step 160).

Rocks are sorted based on grain size distribution (step 162). For example, rocks dominated by fine to medium grain sizes are separated from rocks that include coarse to gravel grain sizes. Fine to medium grain sizes are used as distinct criteria for classification. Method 150 is generally the reverse of a diageneses processes from deep burial to sea floor setting. Method 150 can be programmed in an algorithm and executed on a computer to perform auto-classification.

Figure 3B:
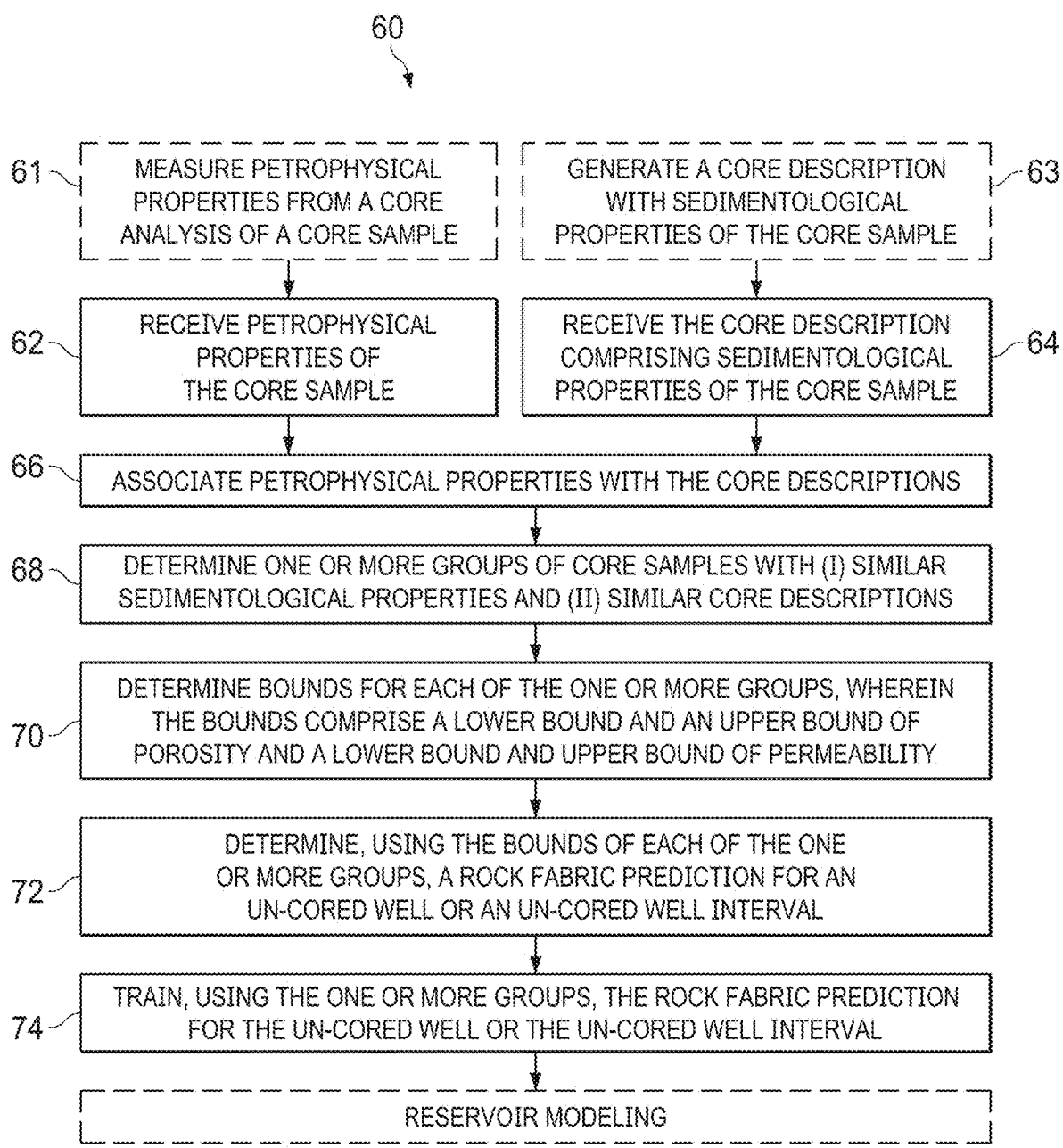
Figure 4:
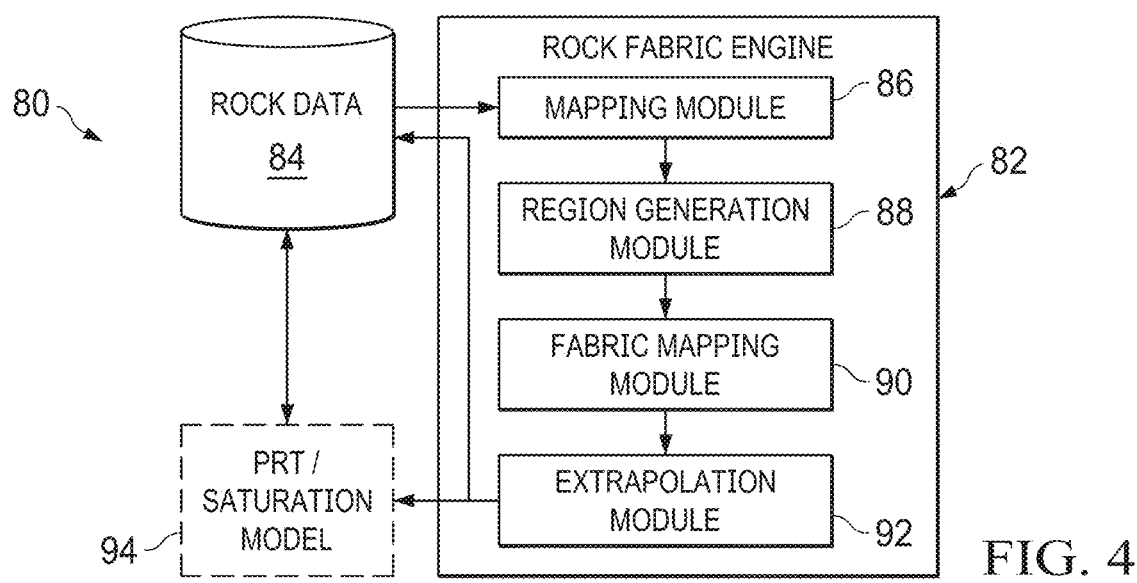
FIG. 4 is schematic of system for performing rock fabric classification.

FIG. 3B presents a flowchart illustrating an example of a method 60 for classifying rock fabric to support modeling hydrocarbon reservoirs. FIG. 4 is schematic of a system 80 for implementing the methods 60 and/or 150.

The method 60 starts with acquiring plug data and a core description (for example, based on Dunham's classification) representing the lithology of a reservoir being modeled or investigated. In some implementations, petrophysical properties including at least permeability and porosity are measured by analysis of core samples (step 61). In some implementations, previously measured petrophysical properties including at least permeability and porosity are received (step 62) by the rock fabric engine 82 of the system 80 from a database 84 storing rock data. In some implementations, a core description is generated, for example, based on observed rock fabrics (step 63). In some implementations, previously recorded core descriptions are received (step 64) by the system 80 from the database 84 storing rock data.

Figure 5A:
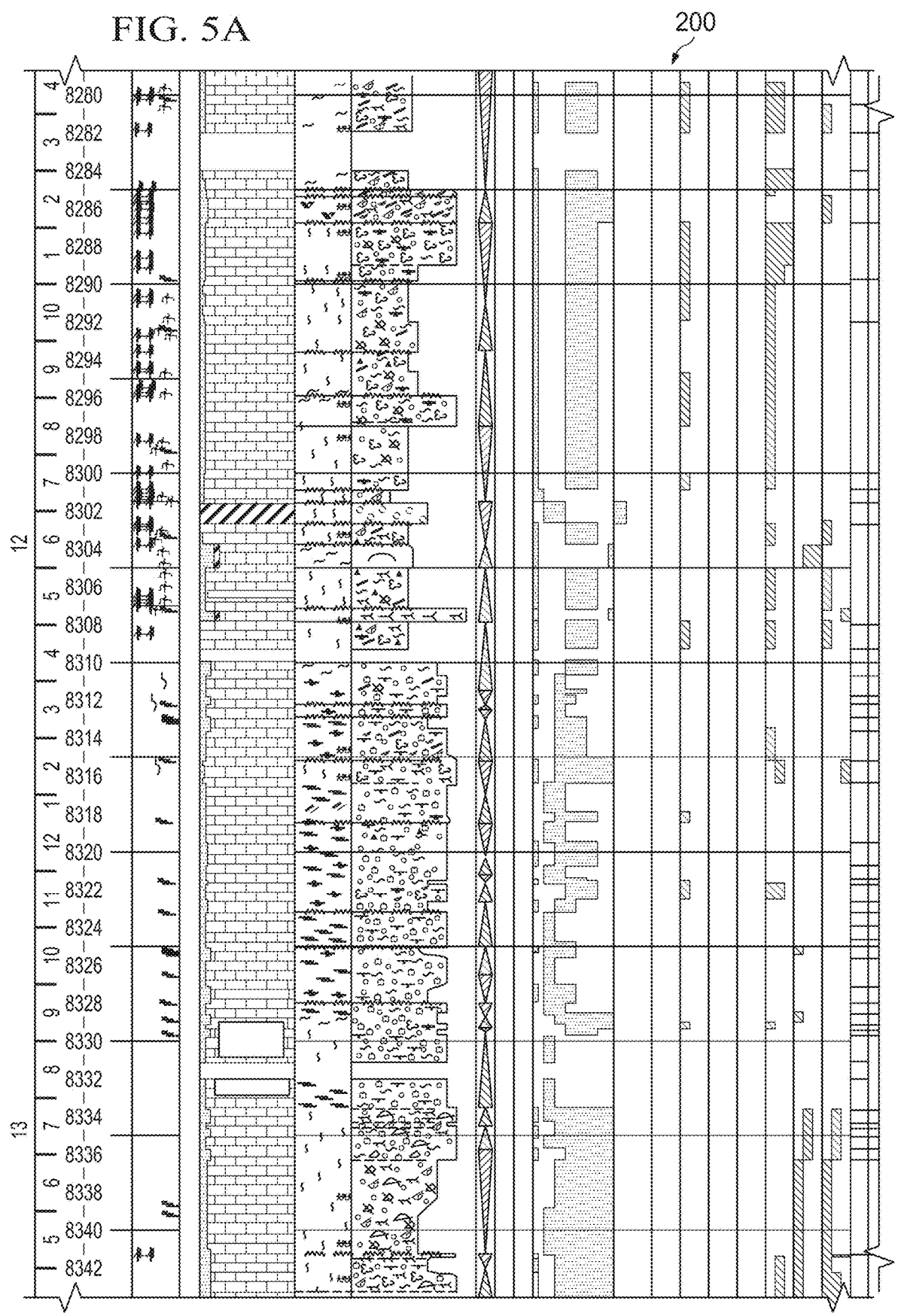
FIG. 5A is an example core description and FIG. 5B is an example of cores that comprise the core description.
Figure 5B:

FIG. 5A is an example core description 200 based on a percentage estimation chart used to aid visual estimation of grains, porosity, and other features. FIG. 5B is an example of trays 250 filled with cores 254 and is used to describe the features of the example core description of FIG. 5A. Mineral composition, sedimentary structures, fracture, and stylolite are also documented. Qualitative sorting is inferred from the different number or wide range of observed grain sizes and this includes skeletal grains, foraminifera, and non-skeletal grains. Stratification is described from the observed sedimentary structures from highly burrowed rock to cross-bedded.

Description of the core 254 begins by measuring and marking the depth of the core 254 associated with each tray 252. The depth of the core is documented and represented along the vertical axis in the core description 200. The observed rock and sedimentological parameters are determined and documented in respective columns in the core description 200. A symbol represents the observed stylolites and fractures of the core 254. An abbreviation for each core 254 represents pore type. Mineral composition of each core 254 represents the percentage of mineral of the rock and includes the pore percentage. Sedimentary structures represent bedding types and bioturbation intensity of the core 254. Symbols are assigned for each type. The texture column includes an outer profile representing the rock texture and symbols representing grain type. Each grain type has a symbol. Triangles reflect the cyclicity in sedimentation. Grain size is documented and shaded based on measured grain size of allochems and presence of mud. Degree of occurrence of fossils is documented. Each column reflects a specific fossil. Color of the rock documented and hydrocarbon staining. The core description 200 includes a column for comments.

Referring again to FIG. 3B and FIG. 4, the data from step 62 and step 64 are combined by a mapping module 86 to form an associated data set (step 66). This can be done by associating the core plug data with the permeability and porosity data based on depth. This association can be done using software, such as Techlog.

The core plug measurements of porosity vs. permeability data are plotted for every Dunham's fabric, where, preferably, every fabric will have its own porosity vs. permeability cross plot and a trend. One or more groups of core samples with (i) similar sedimentological properties and (ii) similar core descriptions are then determined (step 68). Similar lithological parameters are usually manually highlighted from the described core window along with their associated porosity vs. permeability measurements, and related plugs are highlighted on the porosity vs. permeability plot and their measurements.

Figure 6:
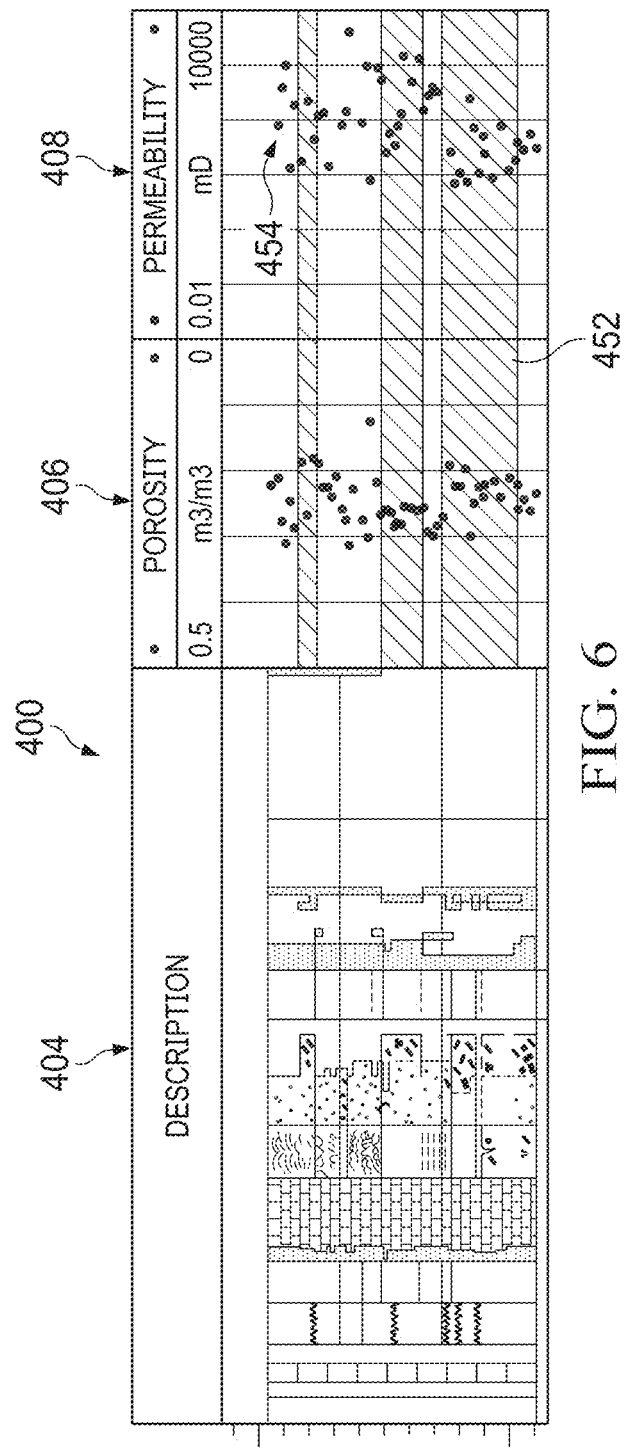
FIG. 6 is an example of a core description with associated permeability and porosity data.
Figure 7:
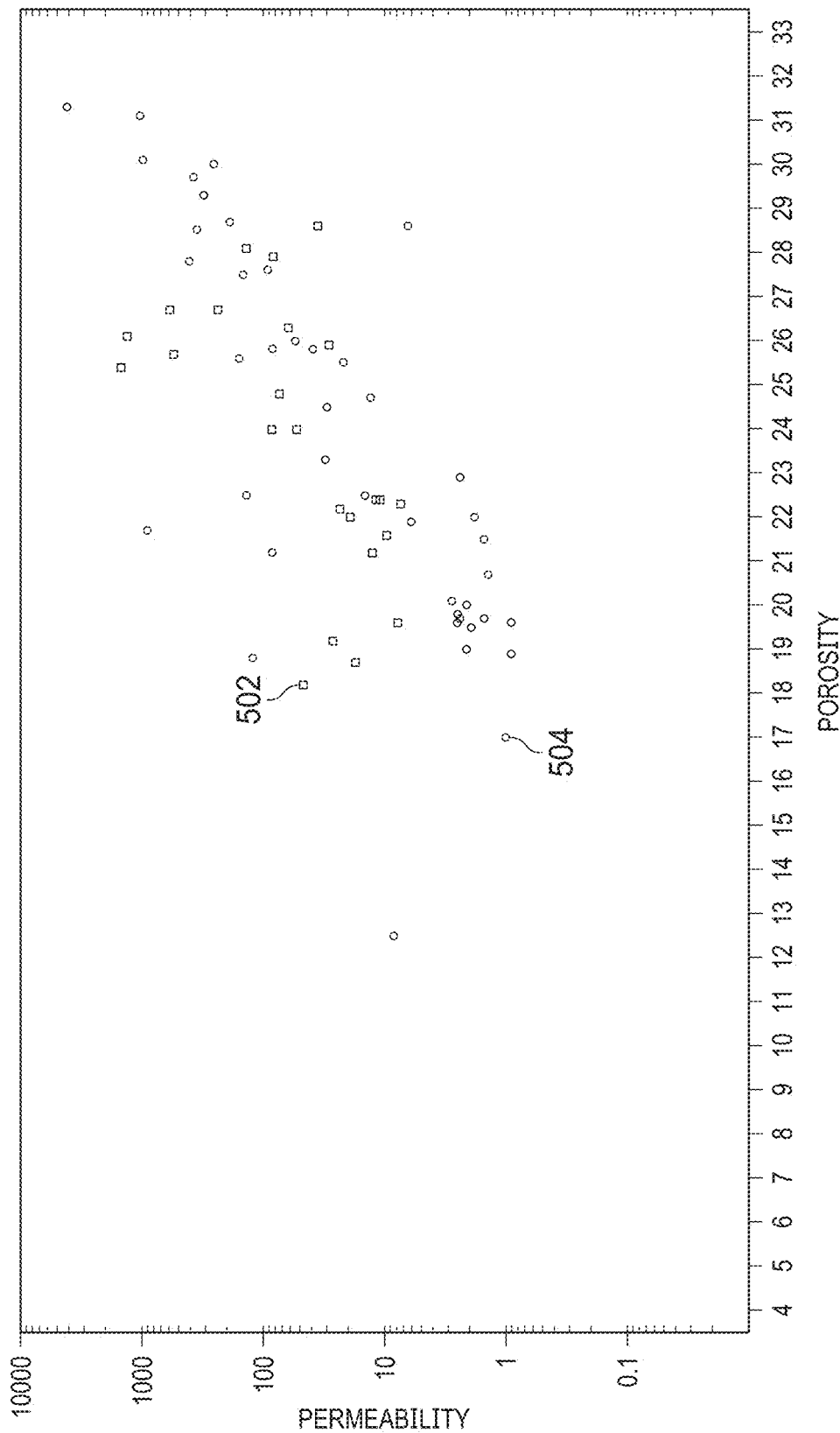
FIG. 7 is a permeability vs. porosity plot.

FIG. 6 is a portion of a core description 400 with similar characteristics to core description 200. By appending a column for porosity 406 and a column for permeability 408 to the column of core descriptions 404, it is possible to observe differences across the columns to assist in the determination of region classifications discussed in more detail with respect to FIG. 7, FIG. 9A, and FIG. 9B. FIG. 7 is a permeability vs. porosity plot of data with similar characteristics to the data shown in FIG. 6. Permeability data is plotted on a logarithmic base-10 scale and porosity data is plotted on a linear scale. While the data shown in FIG. 6 and FIG. 7 use different data sets to illustrate the systems and methods of this specification, generally the same data set is used.

In the core description 400, specific rows with similar lithological parameters can be selected as indicated by the highlighting 452. The highlighted plugs 452 are also highlighted on the permeability vs. porosity cross plot 500 in FIG. 7 with the highlighted rows 452 corresponding to the highlighted markers 502 in FIG. 7. Non-highlighted data 454 in FIG. 6 is seen as non-highlighted 504 in FIG. 7. This allows visualization of the mapping to see if the highlighted rows 452 correspond to clustered regions on the permeability vs. porosity cross plot 500. This process is can be performed manually, by iterating between the core description 400 and the permeability vs. porosity cross plot 500. However, automated methods such as computer implemented scripting languages implemented on system 80 can be used. For example, this process can be performed by utilizing Techlog to accelerate the process. Techlog is a software platform intended to aggregate wellbore information and is used in the oil and gas industry. In some cases, Techlog is used to visualize a 1D core description and a cross plot. However, the systems and methods described in this specification can be used with any software to aggregate and visualize core descriptions and are not limited to Techlog software.

Referring again to FIG. 6 and FIG. 7, regions of one or more groups can be drawn or otherwise established using the clustering of plug data associated with similar sedimentological parameters (step 68) by the region generation module 88. As previously mentioned, plug data resulting from routine core analysis is used in the classification process. This data can include depth, plug number, porosity, and permeability information and can be plotted on the permeability vs. porosity cross plot 500. Bounds are determined for each of the one or more groups which includes a lower bound and an upper bound of porosity and a lower bound and upper bound of permeability (step 70).

Figure 8:
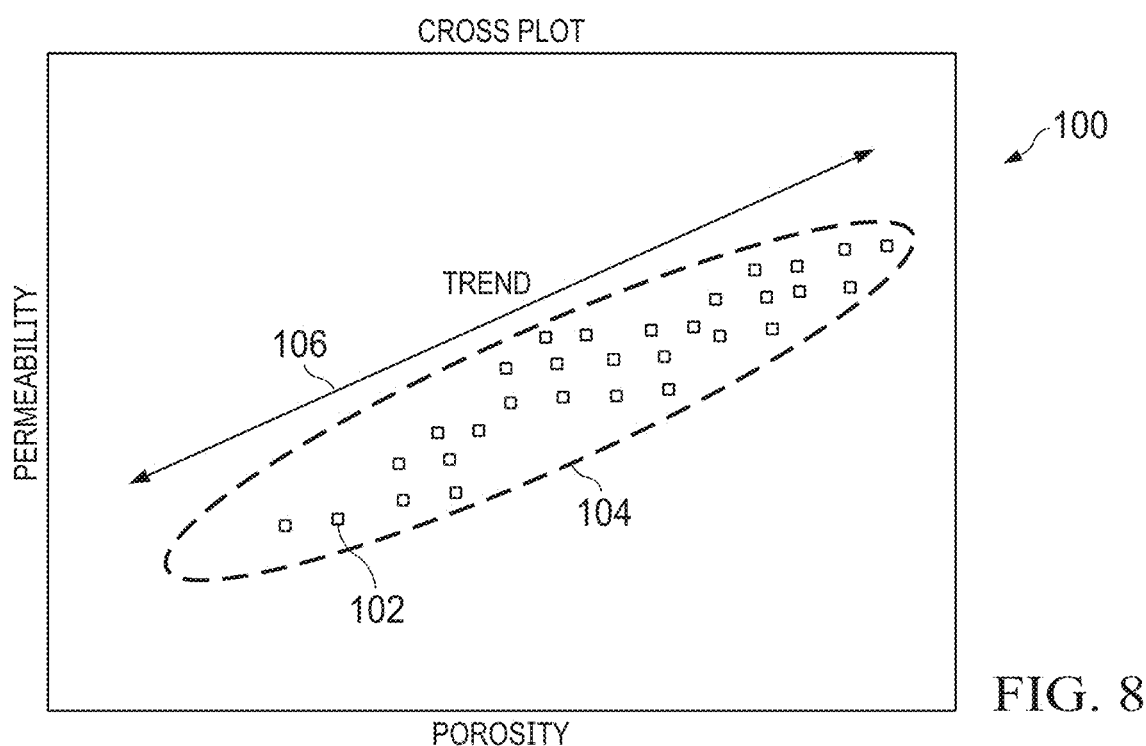
FIG. 8 is a permeability vs. porosity plot of a rock fabric illustrating a classification and trend.

FIG. 8 is an example of a permeability vs. porosity plot 100 of a rock fabric illustrating the typical relationship and trend. Data measurements 102 are plotted on the permeability vs. porosity plot 100 which define statistical groups 104 where a majority of the data measurements 102 exist. Groups 104 typically have a trend 106 that is be used to estimate the permeability vs. porosity properties of the group 104. In addition to providing estimated properties, once the group 104 and the trend 106 are established, these are used to predict permeability vs. porosity bounds for rock fabrics with similar sedimentary parameters. Every rock fabric will show a trend 106 in a porosity vs. permeability plot 100. While it is expected that sedimentary parameters will control the clustering location on the trend 106, the same trend 106 might not result from the same sedimentological parameters.

FIG. 9A shows a permeability vs. porosity cross plot 300 for a grainstone rock fabric from several cored wells. Multiple cores from multiple wells 302, 304, 306 are used to generate the results shown in FIG. 9A. The cores shown belong to the same core interval. Permeability data is plotted on a logarithmic base-10 scale and porosity data is plotted on a linear scale with each well indicated by a different marker. Data from a first well 302 uses circle markers, data from a second well 304 uses square markers, and data from a third well 306 uses diamond markers. All data represents a grainstone rock fabric. A cross-plot for the first well 302 and the second well 304 shows a general clustering of results and a trend is observable. When fit by a linear regression line, the trend line has a finite slope. However, as shown in FIG. 9A, the slope can be different between different reservoirs. The third well 306 does not show a clear clustering, but the general trend is similar to the trend of the first well 302 and second well 304.

FIG. 9A illustrates that sometimes there may be no clustering or grouping for the grainstone rock fabric or texture. The circle markers associated with the first well 302 indicate a wide porosity range and a narrow permeability range due to differences related to sedimentological parameters as previously such as pore types and grain size as previously described. The systems and methods described in this specification assemble groups of similar sedimentological related rocks that otherwise may not indicate a clear clustering.

Figure 10A:
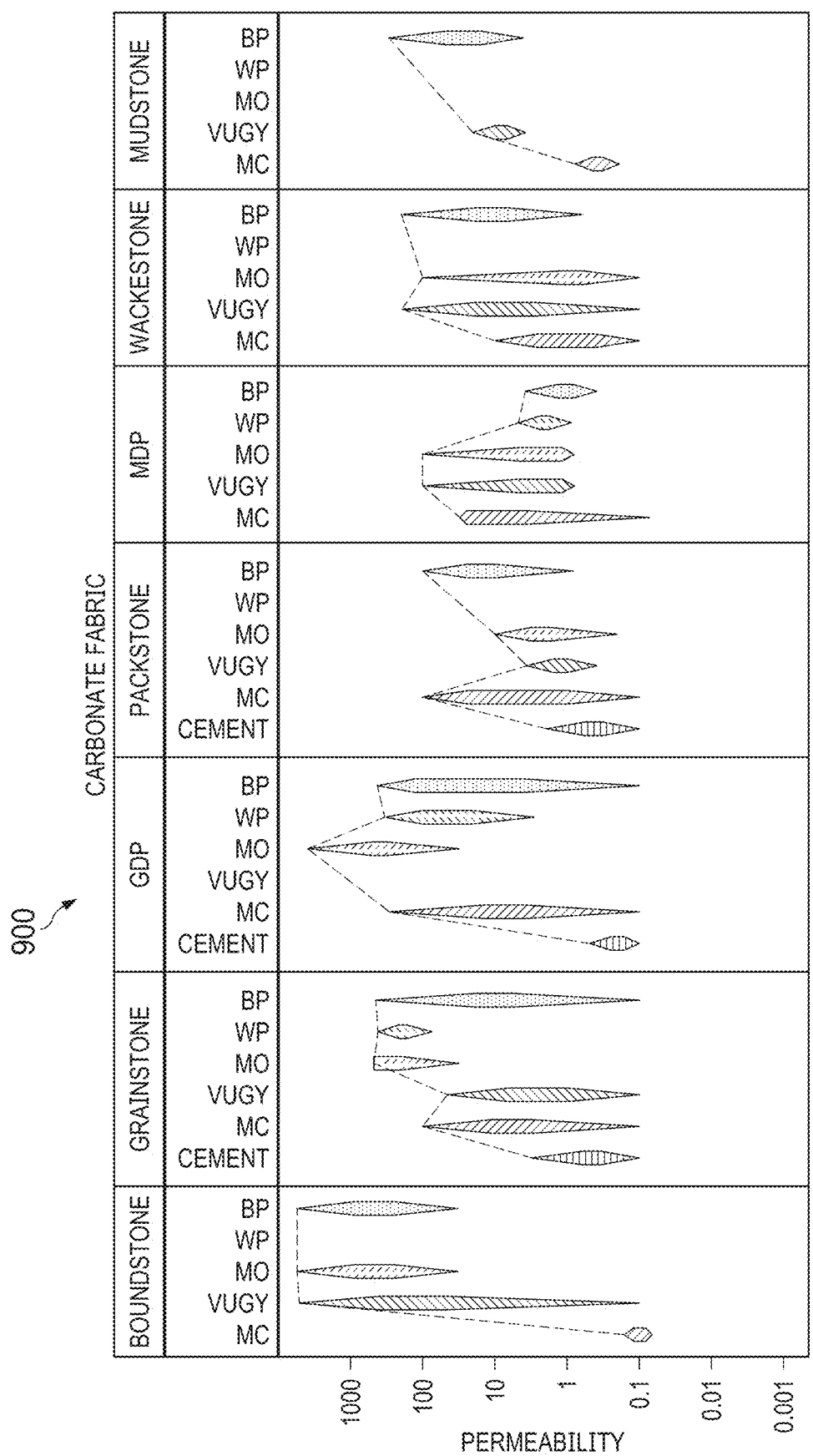
FIGS. 10A-10D are permeability classification charts for carbonite fabrics.

FIGS. 10A-10D are data plots showing the permeability for carbonite fabrics of boundstone, grainstone, GDP, packstone, MDP, wackestone, and mudstone. FIG. 10A is a data plot of the permeability for different pore types 900 of MC, Vugy, MO, VP, and BP for each described fabric. Cement is added in addition to the pore types. The different pore types and cement represent the dissolution and cementation process as part of the diagenesis. As shown in FIG. 10A, cemented intervals have low permeability values compared to intervals associated with the moldic and vugy pore types because of dissolution. Boundstone texture has higher permeability values compared to others.

Figure 10B:
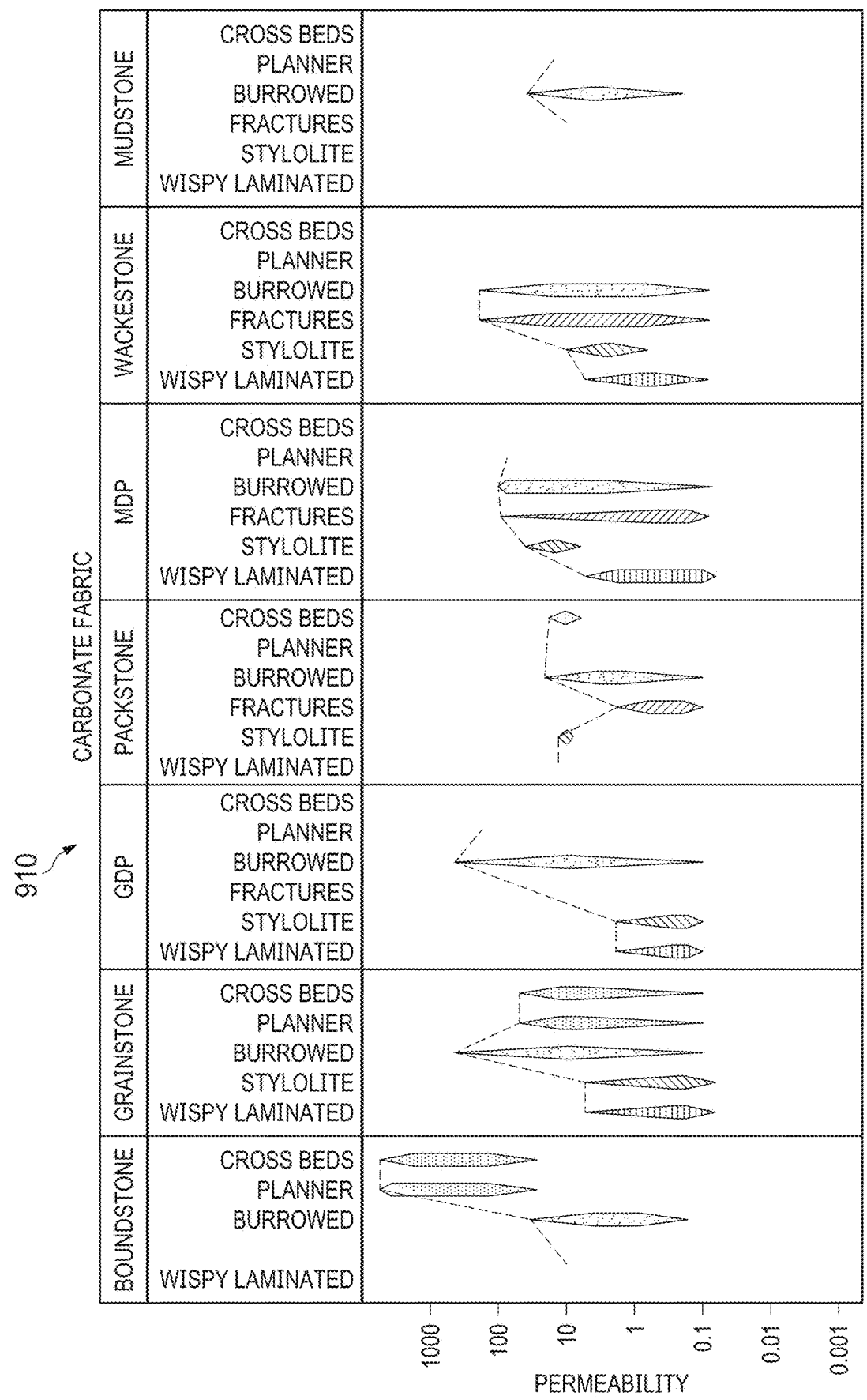

FIG. 10B is a data plot showing the sedimentary structure 910 for the carbonite fabrics shown in FIG. 10A. The sedimentary structures, such as wispy laminated, stylolite, fractures, burrowed, planner, and cross beds, are arranged to reflect the degree in diagenesis with burial. As shown in FIG. 10B, wispy lamination and stylolite rocks have permeability values below 1 mD. This considered a low permeability value. Bioturbation by organisms results in homogenized rocks which is why burrowed rocks have a wide range in permeability. Boundstone has a higher permeability value with a preserved primary sedimentary structure such as cross beds and planner bedding.

Figure 10C:
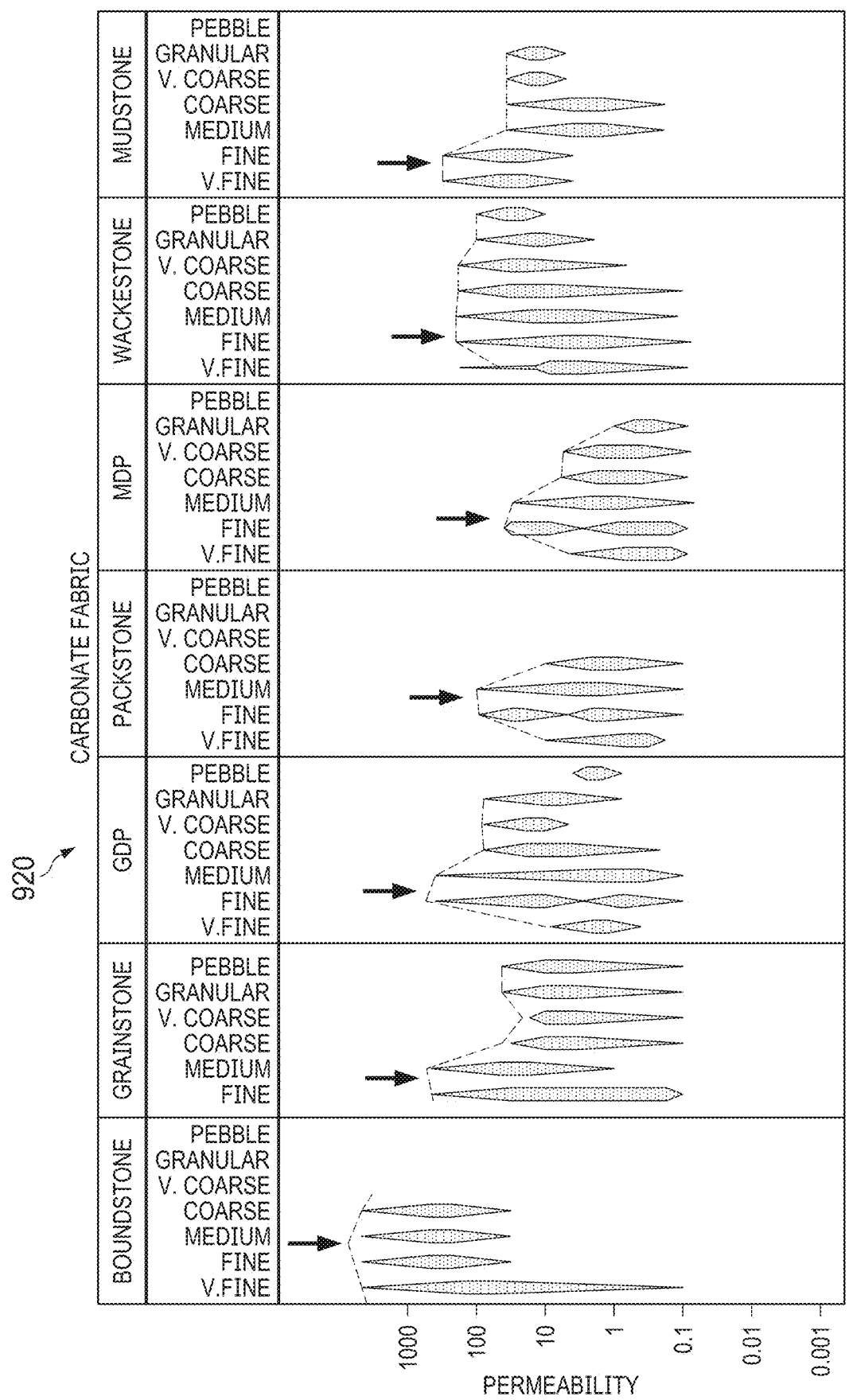
Figure 10D:
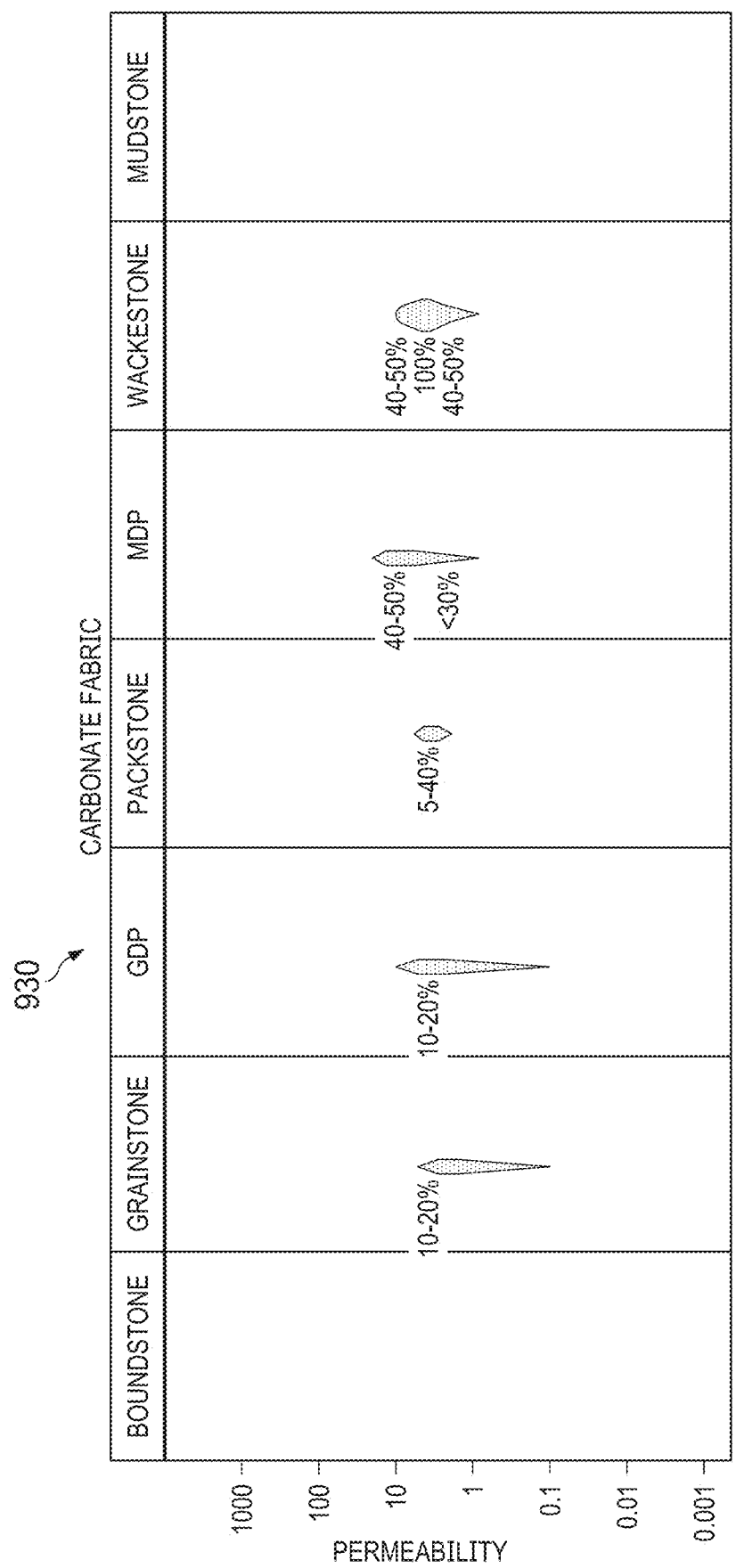

FIG. 10C is a data plot of grain size 920 for the carbonite fabrics shown in FIG. 10A. Grain size is arranged from very fine to pebble size. Notably, fine and medium sizes (each denoted by the arrow) tend to have higher permeability values in each texture. FIG. 10D is a data plot of a dolomitization degree 930 for the carbonite fabrics shown in FIG. 10A. Dolomitization generally is within 1 to 10 mD range, but is observed at 0.1 mD. Dolomitization is sometimes not a good permeability indicator but it is a porosity enhancer.

Taken individual, each of the results shown in FIG. 10A-10D do not indicate a clear separation of each rock texture along the permeability axis from low permeability to high permeability. Most parameters found within 0.1 to 10 mD which is consistent with the range of permeability seen in the cross plot of FIG. 9A. The systems and methods described in this specification aid in combining diagenetic related parameters.

Clusters of data for each analyzed well can be further examined in view of the observed grain size, pore types, stratification, qualitative sorting, and mineral composition. Referring to FIG. 9B, regions 350 are identified around clustered plugs that have similar sedimentological parameters. For example, the data shown in FIGS. 10A-10D aid in determining regions 351-355 which each represent a distinct set of sedimentological parameters. The regions 351-355 represent a statistical result, so some of the well bore data 302, 304, and 306 can lie outside these regions. The similarity of the data within each region can be dominated by any of the sedimentological parameters discussed above.

In this reservoir, there is a major influence of grains size variation on the distribution of data in FIG. 9A and FIG. 9B. The same variation is also apparent with pore types and sedimentary structures. To see the effect of one particular sedimentological parameter, the other sedimentological parameters should remain constant.

Generation of FIGS. 9A and 9B starts by considering each sedimentological feature in FIG. 6. Related plugs with similar rock types are highlighted in FIG. 6. The results of FIG. 6 is compared with the cross plot results of porosity and permeability shown in FIG. 7. Common areas are highlighted in FIG. 9A by iterating between FIG. 6 and FIG. 7 for each set of plug data and each described rock type. After analyzing every well, clusters of data sharing similar and common sedimentological parameters are compiled as shown in FIG. 9B. A letter representing each region or cluster is assigned.

Once this process is complete, and the majority of data is accounted for, the regions can be considered the new sub-classification for the assigned fabric. This is also referred to as a reclassification of the rock fabric. As previously mentioned, the regions of FIG. 9B indicate porosity and permeability bounds for each region. Thus, porosity and permeability bounds can be predicted for rock fabrics with the same or substantially similar sedimentological parameters as the ones in the grouping without expensive porosity and permeability testing (such as MICP testing discussed above).

Once the regions are established, every rock fabric can be subdivided into subclasses and renamed by adding a suffix number to it. In this example, this number represents increasing porosity and permeability values, but any unique identifier can be used. These subclasses can be assigned lower and upper porosity values using the boundary of each region. The permeability and porosity boundaries are used to separate between two partially overlapping clusters of data. If the clusters of data are naturally separated, the use of porosity or permeability boundaries are not necessary. The inclusion of a permeability and porosity boundaries is a user preference.

Tables 1A-1D show representative porosity and permeability bounds for representative regions of an MDP rock fabric along with a description of some common sedimentological parameters present. Similar tables are generated for the other rock fabrics. The trend for every rock fabric and distribution of different groupings/clusters along the trend is a result of these combined features.

TABLE 1A

| Sub-Class | MDP 1 | MDP 1 | MDP 2 | MDP 2 | MDP 3 | MDP 3 | MDP 4 | MDP 4 | MDP 5 | MDP 5 |
|---|---|---|---|---|---|---|---|---|---|---|
| boundary | U | L | U | L | U | L | U | L | U | L |
| porosity | 32 | 26 | 26 | 20 | 20 | 15 | 15 | 10 | 10 | 5 |
| permeability | 20 | 5 | 10 | 0.8 | 5 | 0.3 | 1 | 0.09 | 0.8 | 0.09 |
| Pore Type | MI | MI | MI | MI | MI | MI | MI | MI | MI | MI |
| vugs | | | | | | | | | | |
| WP | | | | | | | | | | |
| MO | | | | | | | | | | |
| MC | 1 | 1 | 1 | 1 | 1 | 1 | 1 | 1 | 1 | 1 |
| BP | | | | | | | | | | |
| Grain Size | Fine | Fine | Fine | Fine | V.fine-m, some c-v.c | V.fine-m, some c-v.c | V.fine-m, some c-v.c | V.fine-m, some c-v.c | fine-m some v.c grains | fine-m some v.c grains |
| M | 1 | 1 | 1 | 1 | 1 | 1 | 1 | 1 | 1 | 1 |
| vf | | | | | 1 | 1 | 1 | 1 | | |
| f | 1 | 1 | 1 | 1 | 1 | 1 | 1 | 1 | 1 | 1 |
| m | | | | | 1 | 1 | 1 | 1 | 1 | 1 |
| c | | | | | 1 | 1 | 1 | 1 | | |
| vc | | | | | 1 | 1 | 1 | 1 | 1 | 1 |
| g | | | | | | | | | | 1 |
| p | | | | | | | | | | |

TABLE 1B

| Sub-Class | MDP 1 | MDP 1 | MDP 2 | MDP 2 | MDP 3 | MDP 3 | MDP 4 | MDP 4 | MDP 5 | MDP 5 |
|---|---|---|---|---|---|---|---|---|---|---|
| Sedimentary structure | mottled, some vertical &H | mottled, some vertical &H | Mottled, wispy, some V&H burrows | Mottled, wispy, some V&H burrows | mottled, wispy, thalasinoides, V&H burrows | mottled, wispy, thalasinoides, V&H burrows | mottled, wispy, thalasinoides, V&H burrows | mottled, wispy, thalasinoides, V&H burrows | wispy, V&H burrows | wispy, V&H burrows |
| Xbeds | | | | | | | | | | |
| Planner | | | | | | | | | | |
| Burrowed | 1 | 1 | 1 | 1 | 1 | 1 | 1 | 1 | 1 | 1 |
| Lamination | | | | | 1 | 1 | 1 | 1 | 1 | 1 |
| Stylolite/Fractures | | | | | | | | | stylolites | stylolites |
| Dolomitzation | 40-50% | 40-50% | 30% | 30% | <30% | <30% | less dolomite | less dolomite | | |
| | | | | | | | | | Argillaceous | Argillaceous |
| Reservoir | B | B | B | B | B | B | B | B | B | B |

TABLE 1C

| Sub-Class | MDP 6 | MDP 6 | MDP 7 | MDP 7 | MDP 1 | MDP 1 | MDP 3 | MDP 3 | MDP 4 | MDP 4 |
|---|---|---|---|---|---|---|---|---|---|---|
| boundary | U | L | U | L | U | L | U | L | U | L |
| porosity | 28 | 23 | 28 | 23 | 16 | 5 | 14 | 7.5 | 21 | 17 |
| permeability | 30 | 6 | 6 | 2 | 1 | 0.8 | 100 | 1 | 4 | 0.4 |
| Pore Type | MO, MI | MO, MI | WP, MO, MI | WP, MO, MI | BP, MO, Vuggy | BP, MO, Vuggy | Vuggy, Mo, BP | Vuggy, Mo, BP | BP | BP |
| vugs |  |  | 1 |  | 1 | 1 | 1 | 1 |  |  |
| WP |  |  |  |  |  |  |  |  |  |  |
| MO | 1 | 1 | 1 | 1 | 1 | 1 | 1 | 1 |  |  |
| MC | 1 | 1 | 1 | 1 |  |  |  |  |  |  |
| BP |  |  |  |  | 1 | 1 | 1 | 1 | 1 | 1 |
| Grain Size | fine-m | fine-m | m-c | m-c | M-granular | M-granular |  |  | Fine | Fine |
| M | 1 | 1 | 1 | 1 | 1 | 1 | 1 | 1 | 1 | 1 |
| vf |  |  |  |  |  |  |  |  |  |  |
| f | 1 | 1 |  |  |  |  |  |  | 1 | 1 |
| m | 1 | 1 | 1 | 1 | 1 | 1 |  |  |  |  |
| c |  |  | 1 | 1 | 1 | 1 |  |  |  |  |
| vc |  |  |  |  | 1 | 1 |  |  |  |  |
| g |  |  |  |  | 1 | 1 |  |  |  |  |
| p |  |  |  |  |  |  |  |  |  |  |

TABLE 1D

| Sub-Class | MDP 6 | MDP 6 | MDP 7 | MDP 7 | MDP 1 | MDP 1 | MDP 3 | MDP 3 | MDP 4 | MDP 4 |
|---|---|---|---|---|---|---|---|---|---|---|
| Sedimentary structure | low bioturbation | low bioturbation | mottled burrow | mottled burrow |  |  | Burrowed | Burrowed |  |  |
| Xbeds Planner |  |  |  |  |  |  |  |  |  |  |
| Burrowed Lamination | 1 | 1 | 1 | 1 |  |  | 1 | 1 |  |  |
| Stylolite/ Fractures | stylolites | stylolites |  |  | Fracture filled with cement | Fracture filled with cement | Fracture filled with cement | Fracture filled with cement |  |  |
| Dolomitzation |  |  |  |  |  |  |  |  |  |  |
|  |  |  |  |  |  |  | Argillaceous | Argillaceous | Argillaceous | Argillaceous |
| Reservoir | B | B | B | B | C | C | C | C | C | C |

Referring again to FIG. 5A and FIG. 6, these regions are considered the new sub-classification or reclassification for the assigned fabric and boundaries for permeability and porosity are established (step 62) by fabric mapping module 90. In particular, a rock fabric prediction for an un-cored well or an un-cored well interval can be determined.

Figure 11:
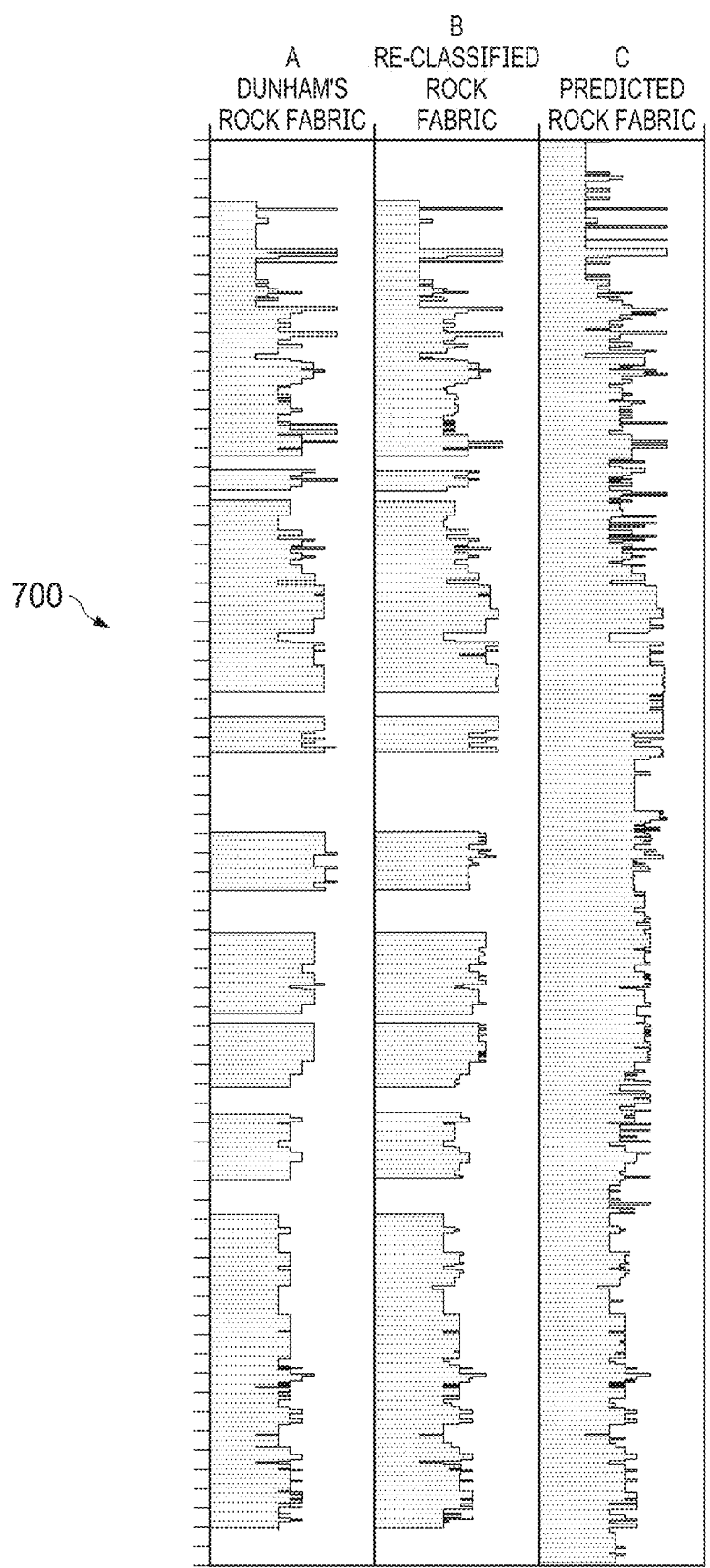
FIG. 11 is an example result of rock fabric re-classification.

FIG. 11 represents new lithofacies curves 700 as a result of this approach that more accurately describes the response in porosity and permeability logs. In FIG. 11, column A is the described Dunham's rock fabric, column B is the re-classified rock fabric based on the sedimentological parameters explained in process 60, and column C is the blind test prediction of the new re-classified fabric as a result of developing and executing a python script and training the data. Importantly, the re-classified rock fabric in cored wells is then used to predict rock fabric in un-cored wells (step 72).

The characteristics of distinct porosity ranges of observed rock fabric and subclasses with distinct porosity ranges can help for mass application on many wells of similar petro-physical response. The reclassification represents the original rock fabric with modified subclasses according to grain size, pore types, stratification, mineral composition, and sorting, as previously mentioned. The application of such subclasses dealing with many sedimentary parameters as variables like grain size, stratification, pore types, and cementation can take a tremendous amount of time. The defined ranges of porosity and permeability for every sub-division can be used as a cutoff to be applied directly on porosity log.

After setting the new classification, data from other sources, for example wireline logs, can be used for the uncored intervals or uncored wells. This process can be conducted on a field scale and not necessarily limited to a specific reservoir. Each reservoir can be divided into several intervals based on sequence stratigraphy for improved consistency and robustness of results.

Referring again to FIGS. 3A-3B and FIG. 4, the process can be trained, using the one or more groups, to predict rock fabric for un-cored wells or un-cored well intervals (step 74) by an extrapolation module 92.

Applying the reclassification to many wells can be time consuming. To enable this, it is possible to use a Python script in Techlog which can be applied on any number of wells. FIG. 12 shows an example of a Python script 850. The inputs are the defined porosity and permeability boundaries as illustrated from the one or more regions, for example from FIG. 6. The Python script will re-code any fabric that belongs to the provided boundaries accordingly. This can be applied on all cored wells at once. The Python script aids in processing and dividing large amounts of described textures based on the defined porosity and permeability values.

This approach requires detail core descriptions according to Dunham's classification, and describing grain size, sorting, pore types, sedimentary structure, dolomitization and other sedimentological features. It assumes that plug data is available, correctly labeled and fitted to core data. This re-classification of rock fabric gives a better understanding of porosity and permeability separation of a reservoir.

The sedimentology and petrophysical properties of a reservoir are important inputs required to build three-dimensional models (petrophysical rock typing (PRT) and saturation modeling). The results of the reclassification can be provided back to the database 84 storing rock data and/or to PRT or saturation models 94 used by petrophysicists to explore and manage a reservoir.

As previously mentioned, individual bias and interpretation is reduced in this approach. This is achieved by presenting the carbonite sedimentological data using the observed rock fabric directly as an input to the models. This helps to reduce and even eliminate any inconsistency and uncertainty due to different interpretations by individual sedimentologists. By using a rock fabric classification, this approach preserves the mud content information and grains packing information in rocks which have a direct effect on the porosity and permeability. Different rock fabric also shows a wide range in porosity and permeability but always shows a trend behavior as illustrated in FIG. 9B. However, this trend and wide range of properties alone is often not sufficient to understand the reservoir or sufficient enough to produce a better petrophysical rock related classification.

The classification can be improved by inclusion of sedimentological parameters into the classification including grain size, sorting, pore type, sedimentary structure, Dolomitization, fracture, and presence of stylolite. Each rock fabric can be observed on the bases of other observed and associated sedimentological features that have an effect on the petrophysical properties.

The disclosed approach helps to identify flow characteristics for each rock fabric by augmenting Dunham's classification with an analysis of core plugs, which is usually available. The disclosed approach is to analyze various trends of the rock fabric in terms of various sedimentological parameters. This approach can also help to identify lithofacies for Mercury Injection Capillary Pressure (MICP) testing by helping to identify intervals that should be analyzed and tested.

Figure 13:
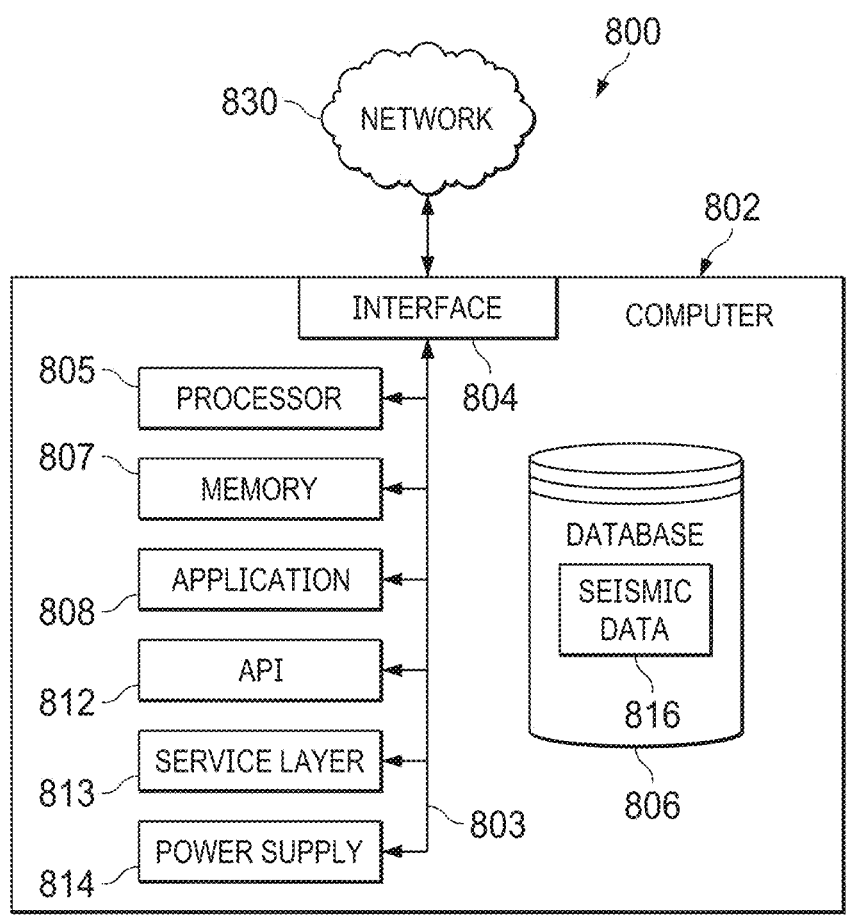
FIG. 13 is a block diagram illustrating an example computer system used to provide computational functionalities associated with described algorithms, methods, functions, processes, flows, and procedures as described in the present disclosure, according to some implementations of the present disclosure.

FIG. 13 is a block diagram of an example computer system 800 used to provide computational functionalities associated with described algorithms, methods, functions, processes, flows, and procedures described in the present disclosure, according to some implementations of the present disclosure. The illustrated computer 802 is intended to encompass any computing device such as a server, a desktop computer, a laptop/notebook computer, a wireless data port, a smart phone, a personal data assistant (PDA), a tablet computing device, or one or more processors within these devices, including physical instances, virtual instances, or both. The computer 802 can include input devices such as keypads, keyboards, and touch screens that can accept user information. Also, the computer 802 can include output devices that can convey information associated with the operation of the computer 802. The information can include digital data, visual data, audio information, or a combination of information. The information can be presented in a graphical user interface (UI) (or GUI).

The computer 802 can serve in a role as a client, a network component, a server, a database, a persistency, or components of a computer system for performing the subject matter described in the present disclosure. The illustrated computer 802 is communicably coupled with a network 830. In some implementations, one or more components of the computer 802 can be configured to operate within different environments, including cloud-computing-based environments, local environments, global environments, and combinations of environments.

At a high level, the computer 802 is an electronic computing device operable to receive, transmit, process, store, and manage data and information associated with the described subject matter. According to some implementations, the computer 802 can also include, or be communicably coupled with, an application server, an email server, a web server, a caching server, a streaming data server, or a combination of servers.

The computer 802 can receive requests over network 830 from a client application (for example, executing on another computer 802). The computer 802 can respond to the received requests by processing the received requests using software applications. Requests can also be sent to the computer 802 from internal users (for example, from a command console), external (or third) parties, automated applications, entities, individuals, systems, and computers.

Each of the components of the computer 802 can communicate using a system bus 803. In some implementations, any or all of the components of the computer 802, including hardware or software components, can interface with each other or the interface 804 (or a combination of both), over the system bus 803. Interfaces can use an application programming interface (API) 812, a service layer 813, or a combination of the API 812 and service layer 813. The API 812 can include specifications for routines, data structures, and object classes. The API 812 can be either computer-language independent or dependent. The API 812 can refer to a complete interface, a single function, or a set of APIs.

The service layer 813 can provide software services to the computer 802 and other components (whether illustrated or not) that are communicably coupled to the computer 802. The functionality of the computer 802 can be accessible for all service consumers using this service layer. Software services, such as those provided by the service layer 813, can provide reusable, defined functionalities through a defined interface. For example, the interface can be software written in JAVA, C++, or a language providing data in extensible markup language (XML) format. While illustrated as an integrated component of the computer 802, in alternative implementations, the API 812 or the service layer 813 can be stand-alone components in relation to other components of the computer 802 and other components communicably coupled to the computer 802. Moreover, any or all parts of the API 812 or the service layer 813 can be implemented as child or sub-modules of another software module, enterprise application, or hardware module without departing from the scope of the present disclosure.

The computer 802 includes an interface 804. Although illustrated as a single interface 804 in FIG. 8, two or more interfaces 804 can be used according to particular needs, desires, or particular implementations of the computer 802 and the described functionality. The interface 804 can be used by the computer 802 for communicating with other systems that are connected to the network 830 (whether illustrated or not) in a distributed environment. Generally, the interface 804 can include, or be implemented using, logic encoded in software or hardware (or a combination of software and hardware) operable to communicate with the network 830. More specifically, the interface 804 can include software supporting one or more communication protocols associated with communications. As such, the network 830 or the hardware of the interface can be operable to communicate physical signals within and outside of the illustrated computer 802.

The computer 802 includes a processor 805. Although illustrated as a single processor 805 in FIG. 8, two or more processors 805 can be used according to particular needs, desires, or particular implementations of the computer 802 and the described functionality. Generally, the processor 805 can execute instructions and can manipulate data to perform the operations of the computer 802, including operations using algorithms, methods, functions, processes, flows, and procedures as described in the present disclosure.

The computer 802 also includes a database 806 that can hold data (for example, seismic data 816) for the computer 802 and other components connected to the network 830 (whether illustrated or not). For example, database 806 can be an in-memory, conventional, or a database storing data consistent with the present disclosure. In some implementations, database 806 can be a combination of two or more different database types (for example, hybrid in-memory and conventional databases) according to particular needs, desires, or particular implementations of the computer 802 and the described functionality. Although illustrated as a single database 806 in FIG. 8, two or more databases (of the same, different, or combination of types) can be used according to particular needs, desires, or particular implementations of the computer 802 and the described functionality. While database 806 is illustrated as an internal component of the computer 802, in alternative implementations, database 806 can be external to the computer 802.

The computer 802 also includes a memory 807 that can hold data for the computer 802 or a combination of components connected to the network 830 (whether illustrated or not). Memory 807 can store any data consistent with the present disclosure. In some implementations, memory 807 can be a combination of two or more different types of memory (for example, a combination of semiconductor and magnetic storage) according to particular needs, desires, or particular implementations of the computer 802 and the described functionality. Although illustrated as a single memory 807 in FIG. 8, two or more memories 807 (of the same, different, or combination of types) can be used according to particular needs, desires, or particular implementations of the computer 802 and the described functionality. While memory 807 is illustrated as an internal component of the computer 802, in alternative implementations, memory 807 can be external to the computer 802.

The application 808 can be an algorithmic software engine providing functionality according to particular needs, desires, or particular implementations of the computer 802 and the described functionality. For example, application 808 can serve as one or more components, modules, or applications. Further, although illustrated as a single application 808, the application 808 can be implemented as multiple applications 808 on the computer 802. In addition, although illustrated as internal to the computer 802, in alternative implementations, the application 808 can be external to the computer 802.

The computer 802 can also include a power supply 814. The power supply 814 can include a rechargeable or non-rechargeable battery that can be configured to be either user- or non-user-replaceable. In some implementations, the power supply 814 can include power-conversion and management circuits, including recharging, standby, and power management functionalities. In some implementations, the power-supply 814 can include a power plug to allow the computer 802 to be plugged into a wall socket or a power source to, for example, power the computer 802 or recharge a rechargeable battery.

There can be any number of computers 802 associated with, or external to, a computer system containing computer 802, with each computer 802 communicating over network 830. Further, the terms "client," "user," and other appropriate terminology can be used interchangeably, as appropriate, without departing from the scope of the present disclosure. Moreover, the present disclosure contemplates that many users can use one computer 802 and one user can use multiple computers 802.

Implementations of the subject matter and the functional operations described in this specification can be implemented in digital electronic circuitry, in tangibly embodied computer software or firmware, in computer hardware, including the structures disclosed in this specification and their structural equivalents, or in combinations of one or more of them. Software implementations of the described subject matter can be implemented as one or more computer programs. Each computer program can include one or more modules of computer program instructions encoded on a tangible, non transitory, computer-readable computer-storage medium for execution by, or to control the operation of, data processing apparatus. Alternatively, or additionally, the program instructions can be encoded in/on an artificially generated propagated signal. The example, the signal can be a machine-generated electrical, optical, or electromagnetic signal that is generated to encode information for transmission to suitable receiver apparatus for execution by a data processing apparatus. The computer-storage medium can be a machine-readable storage device, a machine-readable storage substrate, a random or serial access memory device, or a combination of computer-storage mediums.

The terms "data processing apparatus," "computer," and "electronic computer device" (or equivalent as understood by one of ordinary skill in the art) refer to data processing hardware. For example, a data processing apparatus can encompass all kinds of apparatus, devices, and machines for processing data, including by way of example, a programmable processor, a computer, or multiple processors or computers. The apparatus can also include special purpose logic circuitry including, for example, a central processing unit (CPU), a field programmable gate array (FPGA), or an application specific integrated circuit (ASIC). In some implementations, the data processing apparatus or special purpose logic circuitry (or a combination of the data processing apparatus or special purpose logic circuitry) can be hardware- or software-based (or a combination of both hardware- and software-based). The apparatus can optionally include code that creates an execution environment for computer programs, for example, code that constitutes processor firmware, a protocol stack, a database management system, an operating system, or a combination of execution environments. The present disclosure contemplates the use of data processing apparatuses with or without conventional operating systems, for example, LINUX, UNIX, WINDOWS, MAC OS, ANDROID, or IOS.

A computer program, which can also be referred to or described as a program, software, a software application, a module, a software module, a script, or code, can be written in any form of programming language. Programming languages can include, for example, compiled languages, interpreted languages, declarative languages, or procedural languages. Programs can be deployed in any form, including as stand-alone programs, modules, components, subroutines, or units for use in a computing environment. A computer program can, but need not, correspond to a file in a file system. A program can be stored in a portion of a file that holds other programs or data, for example, one or more scripts stored in a markup language document, or in a single file dedicated to the program in question, or in multiple coordinated files storing one or more modules, sub programs, or portions of code. A computer program can be deployed for execution on one computer or on multiple computers that are located, for example, at one site or distributed across multiple sites that are interconnected by a communication network. While portions of the programs illustrated in the various figures may be shown as individual modules that implement the various features and functionality through various objects, methods, or processes, the programs can instead include a number of sub-modules, third-party services, components, and libraries. Conversely, the features and functionality of various components can be combined into single components as appropriate. Thresholds used to make computational determinations can be statically, dynamically, or both statically and dynamically determined.

The methods, processes, or logic flows described in this specification can be performed by one or more programmable computers executing one or more computer programs to perform functions by operating on input data and generating output. The methods, processes, or logic flows can also be performed by, and apparatus can also be implemented as, special purpose logic circuitry, for example, a CPU, an FPGA, or an ASIC.

Computers suitable for the execution of a computer program can be based on one or more of general and special purpose microprocessors and other kinds of CPUs. The elements of a computer are a CPU for performing or executing instructions and one or more memory devices for storing instructions and data. Generally, a CPU can receive instructions and data from (and write data to) a memory. A computer can also include, or be operatively coupled to, one or more mass storage devices for storing data. In some implementations, a computer can receive data from, and transfer data to, the mass storage devices including, for example, magnetic, magneto optical disks, or optical disks. Moreover, a computer can be embedded in another device, for example, a mobile telephone, a personal digital assistant (PDA), a mobile audio or video player, a game console, a global positioning system (GPS) receiver, or a portable storage device such as a universal serial bus (USB) flash drive.

Computer readable media (transitory or non-transitory, as appropriate) suitable for storing computer program instructions and data can include all forms of permanent/non-permanent and volatile/non-volatile memory, media, and memory devices. Computer readable media can include, for example, semiconductor memory devices such as random access memory (RAM), read only memory (ROM), phase change memory (PRAM), static random access memory (SRAM), dynamic random access memory (DRAM), erasable programmable read-only memory (EPROM), electrically erasable programmable read-only memory (EEPROM), and flash memory devices. Computer readable media can also include, for example, magnetic devices such as tape, cartridges, cassettes, and internal/removable disks. Computer readable media can also include magneto optical disks and optical memory devices and technologies including, for example, digital video disc (DVD), CD ROM, DVD+/−R, DVD-RAM, DVD-ROM, HD-DVD, and BLU-RAY. The memory can store various objects or data, including caches, classes, frameworks, applications, modules, backup data, jobs, web pages, web page templates, data structures, database tables, repositories, and dynamic information. Types of objects and data stored in memory can include parameters, variables, algorithms, instructions, rules, constraints, and references. Additionally, the memory can include logs, policies, security or access data, and reporting files. The processor and the memory can be supplemented by, or incorporated in, special purpose logic circuitry.

Implementations of the subject matter described in the present disclosure can be implemented on a computer having a display device for providing interaction with a user, including displaying information to (and receiving input from) the user. Types of display devices can include, for example, a cathode ray tube (CRT), a liquid crystal display (LCD), a light-emitting diode (LED), and a plasma monitor. Display devices can include a keyboard and pointing devices including, for example, a mouse, a trackball, or a trackpad. User input can also be provided to the computer through the use of a touchscreen, such as a tablet computer surface with pressure sensitivity or a multi-touch screen using capacitive or electric sensing. Other kinds of devices can be used to provide for interaction with a user, including to receive user feedback including, for example, sensory feedback including visual feedback, auditory feedback, or tactile feedback. Input from the user can be received in the form of acoustic, speech, or tactile input. In addition, a computer can interact with a user by sending documents to, and receiving documents from, a device that is used by the user. For example, the computer can send web pages to a web browser on a user's client device in response to requests received from the web browser.

The term "graphical user interface," or "GUI," can be used in the singular or the plural to describe one or more graphical user interfaces and each of the displays of a particular graphical user interface. Therefore, a GUI can represent any graphical user interface, including, but not limited to, a web browser, a touch screen, or a command line interface (CLI) that processes information and efficiently presents the information results to the user. In general, a GUI can include a plurality of user interface (UI) elements, some or all associated with a web browser, such as interactive fields, pull-down lists, and buttons. These and other UI elements can be related to or represent the functions of the web browser.

Implementations of the subject matter described in this specification can be implemented in a computing system that includes a back end component, for example, as a data server, or that includes a middleware component, for example, an application server. Moreover, the computing system can include a front-end component, for example, a client computer having one or both of a graphical user interface or a Web browser through which a user can interact with the computer. The components of the system can be interconnected by any form or medium of wireline or wireless digital data communication (or a combination of data communication) in a communication network. Examples of communication networks include a local area network (LAN), a radio access network (RAN), a metropolitan area network (MAN), a wide area network (WAN), Worldwide Interoperability for Microwave Access (WIMAX), a wireless local area network (WLAN) (for example, using 802.11 a/b/g/n or 802.20 or a combination of protocols), all or a portion of the Internet, or any other communication system or systems at one or more locations (or a combination of communication networks). The network can communicate with, for example, Internet Protocol (IP) packets, frame relay frames, asynchronous transfer mode (ATM) cells, voice, video, data, or a combination of communication types between network addresses.

The computing system can include clients and servers. A client and server can generally be remote from each other and can typically interact through a communication network. The relationship of client and server can arise by virtue of computer programs running on the respective computers and having a client-server relationship.

Cluster file systems can be any file system type accessible from multiple servers for read and update. Locking or consistency tracking may not be necessary since the locking of exchange file system can be done at application layer. Furthermore, Unicode data files can be different from non-Unicode data files.

While this specification contains many specific implementation details, these should not be construed as limitations on the scope of what may be claimed, but rather as descriptions of features that may be specific to particular implementations. Certain features that are described in this specification in the context of separate implementations can also be implemented, in combination, in a single implementation. Conversely, various features that are described in the context of a single implementation can also be implemented in multiple implementations, separately, or in any suitable sub-combination. Moreover, although previously described features may be described as acting in certain combinations and even initially claimed as such, one or more features from a claimed combination can, in some cases, be excised from the combination, and the claimed combination may be directed to a sub-combination or variation of a sub-combination.

Particular implementations of the subject matter have been described. Other implementations, alterations, and permutations of the described implementations are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations may be considered optional), to achieve desirable results. In certain circumstances, multitasking or parallel processing (or a combination of multitasking and parallel processing) may be advantageous and performed as deemed appropriate.

Moreover, the separation or integration of various system modules and components in the previously described implementations should not be understood as requiring such separation or integration in all implementations, and it should be understood that the described program components and systems can generally be integrated together in a single software product or packaged into multiple software products.

Accordingly, the previously described example implementations do not define or constrain the present disclosure. Other changes, substitutions, and alterations are also possible without departing from the spirit and scope of the present disclosure.

Furthermore, any claimed implementation is considered to be applicable to at least a computer-implemented method; a non-transitory, computer-readable medium storing computer-readable instructions to perform the computer-implemented method; and a computer system comprising a computer memory interoperably coupled with a hardware processor configured to perform the computer-implemented method or the instructions stored on the non-transitory, computer-readable medium.

A number of embodiments of the systems and methods have been described. Nevertheless, it will be understood that various modifications may be made without departing from the spirit and scope of this disclosure. Accordingly, other embodiments are within the scope of the following claims.

What is claimed is:

1. A method for modeling subterranean formation using a rock fabric classification, the method comprising:
    receiving petrophysical properties from a core analysis of a plurality of core samples from a wellbore, wherein the petrophysical properties comprise a porosity, a permeability, and a depth of the plurality of core samples;
    receiving a core description of each core sample of the plurality of core samples, the core description comprising sedimentological properties comprising a grain size and a mud to grain fraction of the respective core sample;
    using Dunham's classification to determine a rock fabric of each core sample based on the mud to grain fraction of each respective core description such that a plurality of rock fabrics are determined and a subset of the plurality of core samples are associated with one of the determined rock fabrics;
    sorting each core sample into one of at least two grain size groups based on the grain size of each respective core description;
    generating a separate data set for each determined different rock fabric, the data set comprising the porosities, permeabilities, and grain size group for each core sample associated with the respective rock fabric of the data set, and for each data set:
        determining one or more groups of core samples associated with the respective rock fabric of the data set such that each group has a non-overlapping range of porosities, a non-overlapping range of permeabilities, and each sample of the respective group is associated with a common grain size group;
        determining bounds of each group of the one or more groups based on the non-overlapping range of porosities and the non-overlapping range of permeabilities, wherein the bounds comprise a lower bound and an upper bound of porosity and a lower bound and upper bound of permeability; and
    providing the bounds and an identifier of each of the one or more groups, as input to a model for petrophysical rock typing or saturation modeling.

2. The method of claim 1, further comprising determining, using the bounds of each of the one or more groups, a rock fabric prediction for an un-cored well or an un-cored well interval.

3. The method of claim 2, further comprising training, using the one or more groups, the rock fabric prediction for the un-cored well or the un-cored well interval.

4. The method of claim 1, further comprising, after using Dunham's classification to determine a rock fabric and after sorting each core sample into one of at least two grain size groups, updating the determined rock fabric of the respective core sample as a mud-dominate packstone if the respective core sample (i) comprises grains with the grain size of less a grain size threshold and (ii) comprises the mud to grain fraction in an amount greater than a mud threshold.

5. The method of claim 4, wherein the grain size threshold is less than 1 mm.

6. The method of claim 4, wherein the mud threshold is less than 20%.

7. The method of claim 4, further comprising, after using Dunham's classification to determine a rock fabric and after sorting each core sample into one of at least two grain size groups, updating the determined rock fabric of the respective core sample as a grain-dominated packstone if the respective core sample (i) comprises grains with the grain size of greater than the grain size threshold and (ii) comprises the mud to grain fraction in an amount less than the mud threshold.

8. The method of claim 1, wherein the plurality of core samples represent at least two different lithologies of the wellbore.

9. The method of claim 1, comprising extracting the plurality of core samples from a plurality of wellbores.

10. A system for modeling subterranean formation using a rock fabric classification, the system comprising:
memory that stores information of a plurality of core samples from one or more wellbores, the information comprising petrophysical properties and a core description comprising sedimentological properties;
one or more processing devices configured to access the information of the plurality of core samples of the one or more wellbores, the one or more processing devices further configured to perform actions comprising:
receiving the petrophysical properties comprising a porosity, a permeability, and a depth of each core sample of the plurality of core samples of each core sample of the plurality of core samples;
receiving the core description of each core sample of the plurality of core samples, the core description comprising the sedimentological properties, wherein the sedimentological properties comprise a grain size and a mud to grain fraction of each core sample of the plurality of core samples;
using Dunham's classification to determine a rock fabric of each core sample based on the mud to grain fraction of each respective core description such that a plurality of rock fabrics are determined and a subset of the plurality of core samples are associated with one of the determined rock fabrics;
sorting each core sample into one of at least two grain size groups based on the grain size of each respective core description;
generating a separate data set for each determined different rock fabric, the data set comprising the porosities, permeabilities, and grain size group for each core sample associated with the respective rock fabric of the data set, and for each data set:
determining one or more groups of core samples associated with the respective rock fabric of the data set such that each group has a non-overlapping range of porosities a non-overlapping range of permeabilities, and each sample of the respective group is associated with a common grain size group;
determining bounds of each group of the one or more groups based on the non-overlapping range of porosities and the non-overlapping range of permeabilities, wherein the bounds comprise a lower bound and an upper bound of porosity and a lower bound and upper bound of permeability; and
providing the bounds and an identifier of each of the one or more groups, as input to a model for petrophysical rock typing or saturation modeling.

11. The system of claim 10, wherein the one or more processing devices are further configured to determine, using the bounds of each of the one or more groups, a rock fabric prediction for an un-cored well or an un-cored well interval.

12. The system of claim 11, wherein the one or more processing devices are further configured to train, using the one or more groups, the rock fabric prediction for the un-cored well or the un-cored well interval.

13. The system of claim 11, wherein the one or more processing devices are further configured to perform operations comprising, after using Dunham's classification to determine a rock fabric and after sorting each core sample into one of at least two grain size groups, update the determined rock fabric of the respective core sample as a mud-dominate packstone if the respective core sample (i) comprises grains with the grain size of less a grain size threshold and (ii) comprises the mud to grain fraction in an amount greater than a mud threshold.

14. The system of claim 13, wherein the one or more processing devices are further configured to perform operations comprising, after using Dunham's classification to determine a rock fabric and after sorting each core sample into one of at least two grain size groups, update the determined rock fabric of the respective core sample as a grain-dominated packstone if the core sample (i) comprises grains with the grain size of greater than the grain size threshold and (ii) comprises the mud to grain fraction in an amount less than the mud threshold.

15. The system of claim 10, wherein the plurality of core samples represent at least two different lithologies of the one or more wellbores.

16. The system of claim 10, further comprising a display configured to display the bounds and the identifier of each of the one or more groups.

17. The method of claim 1, comprising determining the rock fabric as one of mudstone, wackestone, packstone, grainstone, boundstone, or crystalline carbonate.

18. The method of claim 1, wherein sorting each core sample into one of at least two grain size groups is performed after using Dunham's classification to determine the rock fabric of each core sample.

19. The method of claim 1, comprising plotting each separate data set on a porosity-permeability cross-plot, and using the porosity-permeability cross-plot to determine the one or more groups of core samples such that each group is non-overlapping when viewed on the respective porosity-permeability cross-plot.

20. The method of claim 1, wherein the sedimentological properties include compaction properties of the core samples and the method further comprises, before sorting each core sample into one of at least two grain size groups, sorting each of the one or more core samples into one of at least two compaction groups based on the compaction properties of each respective core description.

21. The method of claim 20, wherein determining the one or more groups of core samples associated with the respective rock fabric of the data set comprises determining the one or more groups such that each group is associated with a common compaction group.

22. The method of claim 1, wherein the sedimentological properties include cementation properties of the core samples and the method further comprises, after sorting each of the one or more core samples into at least two compaction groups and before sorting each core sample into one of at least two grain size groups, sorting each of the one or more core samples into one of at least two cementation groups based on the cementation properties of each respective core description.

23. The method of claim 22, wherein determining the one or more groups of core samples associated with the respective rock fabric of the data set comprises determining the non-overlapping groups such that each non-overlapping group is associated with a common cementation group.

* * * * *